(12) United States Patent
Self et al.

(10) Patent No.: US 10,188,347 B2
(45) Date of Patent: Jan. 29, 2019

(54) ENERGY EXPENDITURE DEVICE

(71) Applicant: NIKE, Inc., Beaverton, OR (US)

(72) Inventors: Christina S. Self, Portland, OR (US); Kristen L. White, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 1114 days.

(21) Appl. No.: 14/465,485

(22) Filed: Aug. 21, 2014

(65) Prior Publication Data

US 2015/0057942 A1  Feb. 26, 2015

Related U.S. Application Data

(60) Provisional application No. 61/869,499, filed on Aug. 23, 2013.

(51) Int. Cl.
| | |
|---|---|
| A61B 5/00 | (2006.01) |
| G06F 19/00 | (2018.01) |
| A43B 3/00 | (2006.01) |
| A61B 5/11 | (2006.01) |
| A61B 5/103 | (2006.01) |

(52) U.S. Cl.
CPC .......... *A61B 5/4866* (2013.01); *A43B 3/0005* (2013.01); *A61B 5/0024* (2013.01); *A61B 5/486* (2013.01); *A61B 5/7278* (2013.01); *A61B 5/743* (2013.01); *G06F 19/3481* (2013.01); *A61B 5/002* (2013.01); *A61B 5/0022* (2013.01); *A61B 5/1038* (2013.01); *A61B 5/1112* (2013.01); *A61B 5/1118* (2013.01); *A61B 5/1123* (2013.01); *A61B 5/6807* (2013.01); *A61B 5/6824* (2013.01); *A61B 5/6895* (2013.01); *A61B 5/6898* (2013.01); *A61B 5/742* (2013.01); *A61B 5/7475* (2013.01)

(58) Field of Classification Search
CPC .................................................. A61B 5/4866
USPC .......................................................... 434/247
See application file for complete search history.

(56) References Cited

U.S. PATENT DOCUMENTS

| | | | | |
|---|---|---|---|---|
| 2008/0288200 | A1* | 11/2008 | Noble ................ | A61B 5/1116 702/96 |
| 2011/0054359 | A1* | 3/2011 | Sazonov ............. | A43B 3/0005 600/595 |
| 2012/0183939 | A1* | 7/2012 | Aragones ........... | A63B 24/0006 434/247 |

(Continued)

FOREIGN PATENT DOCUMENTS

WO   2006042415 A1   4/2006

OTHER PUBLICATIONS

Jan. 7, 2015—ISR and WO—App. No. PCT/US2014/052226.

*Primary Examiner* — Thomas Hong
(74) *Attorney, Agent, or Firm* — Banner & Witcoff, Ltd.

(57) ABSTRACT

Athletic activity may be tracked and monitored while providing encouragement and maintaining an individual's interest in continuing to perform athletic activity. For example, energy expenditure values and energy expenditure intensity values may be calculated based on the duration and type of activity performed by an individual. These values and other movement data may be displayed on an interface in a manner to motivate the individual and maintain the individual's interest. Other individuals (e.g., friends) may also be displayed on an interface through which a user's progress is tracked. This may allow the user to also view the other individuals' progress toward completing an activity goal and/or challenge.

17 Claims, 19 Drawing Sheets

(56) References Cited

U.S. PATENT DOCUMENTS

2013/0132028 A1 5/2013 Crankson et al.
2013/0191034 A1 7/2013 Weast et al.

* cited by examiner

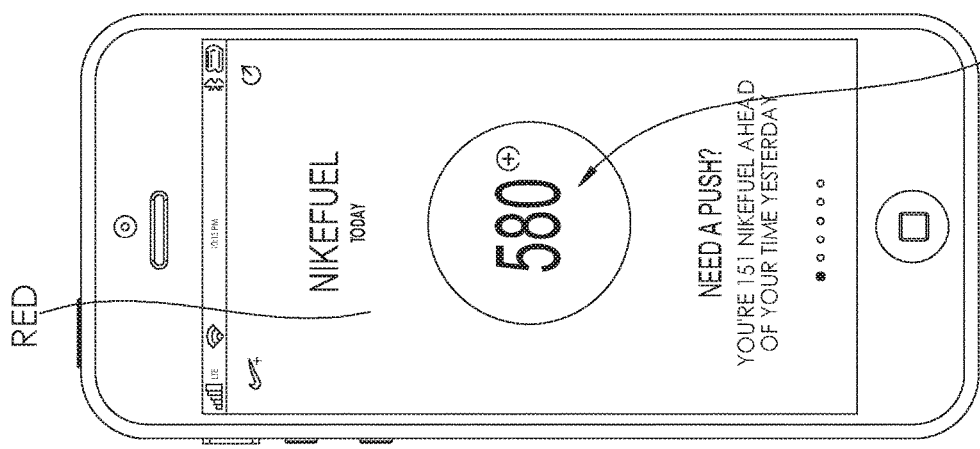
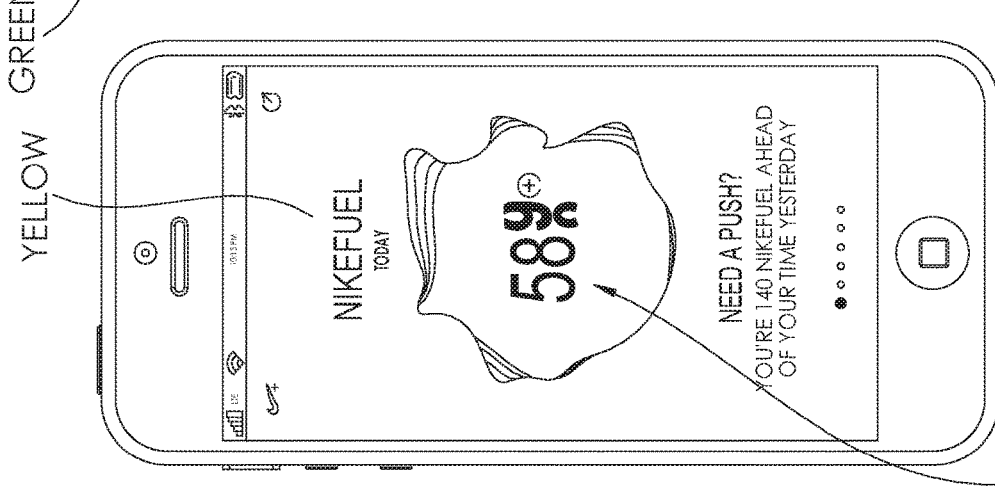
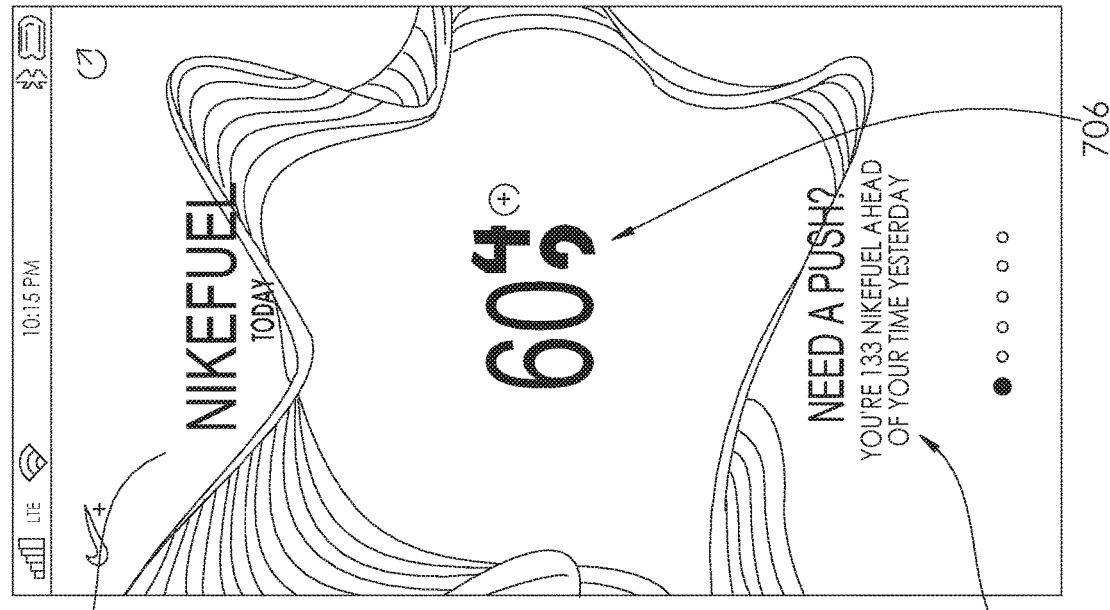
FIG. 7

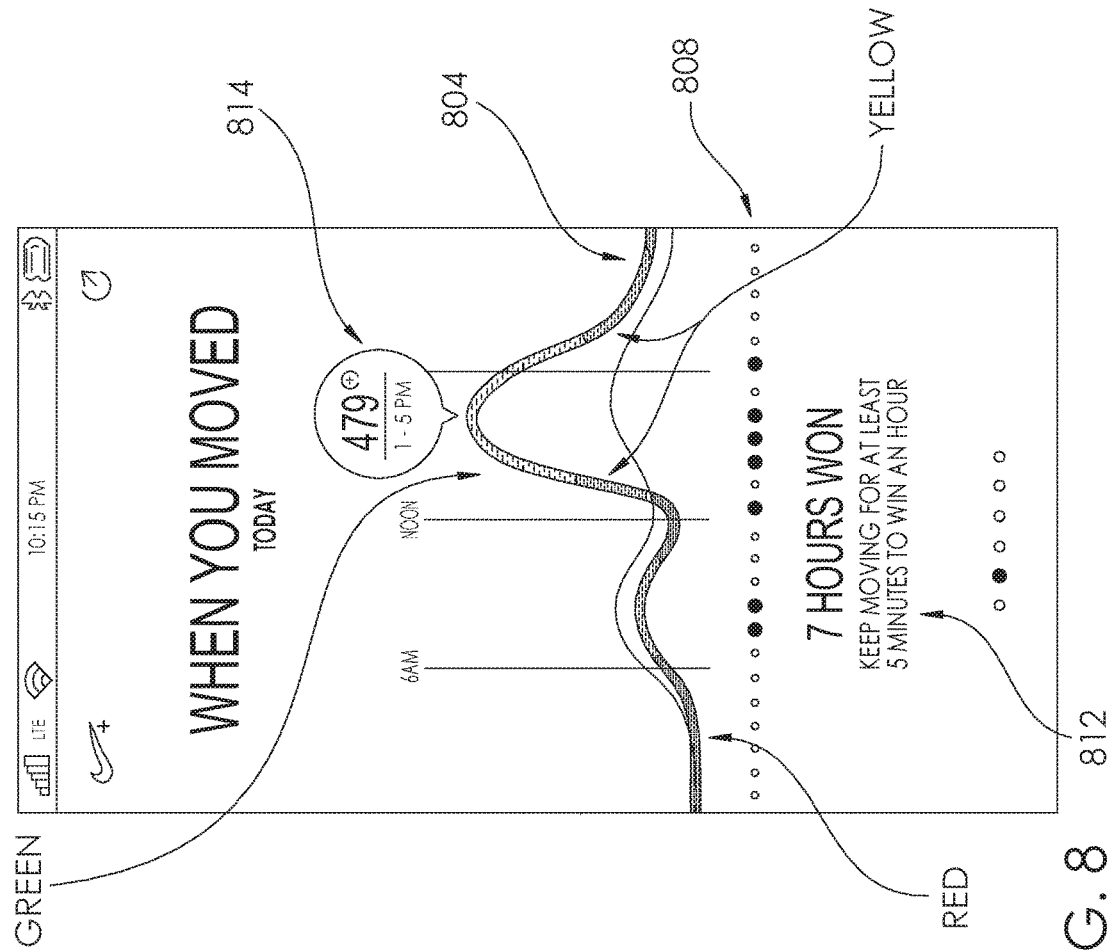
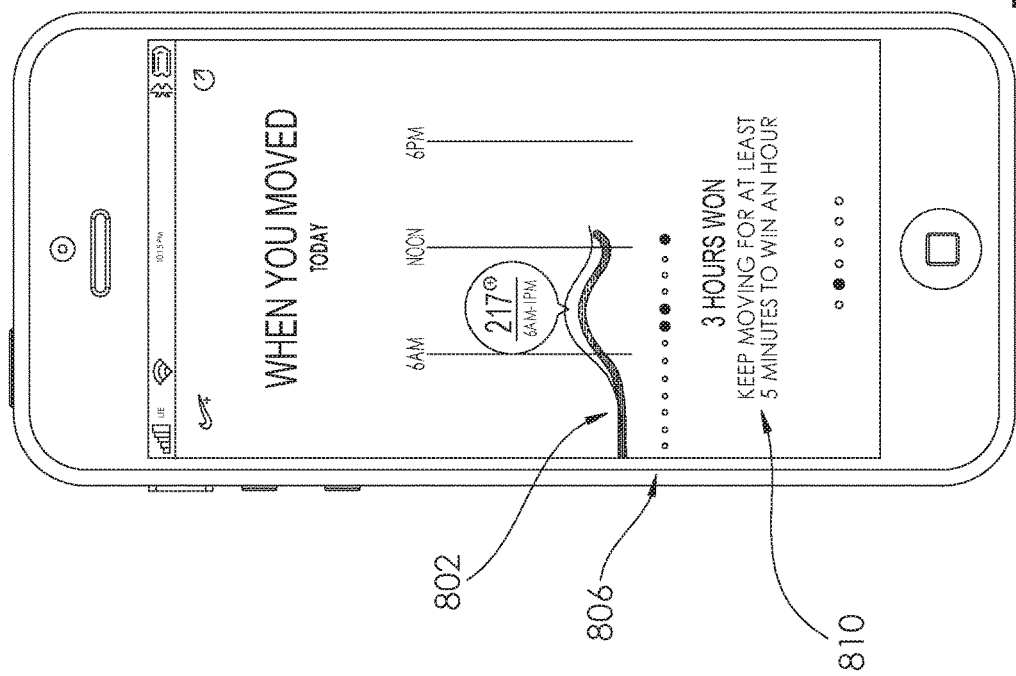
FIG. 8

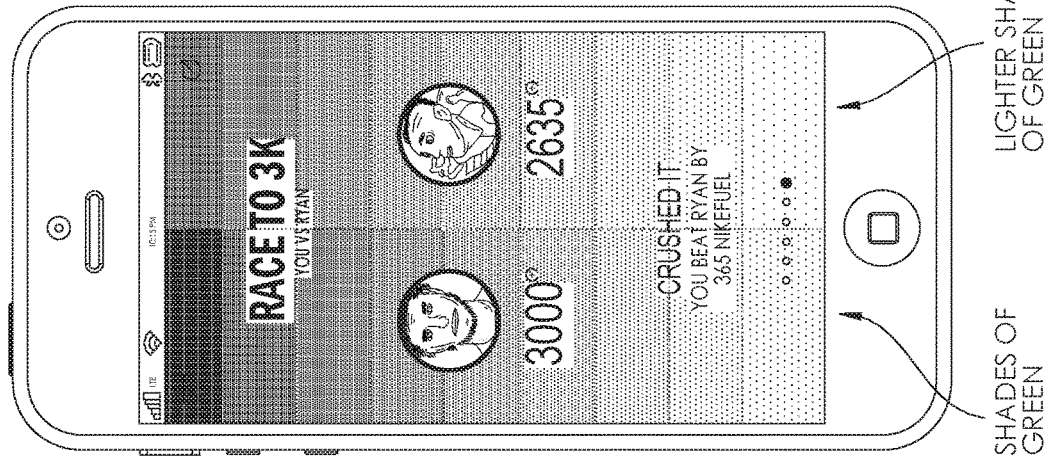
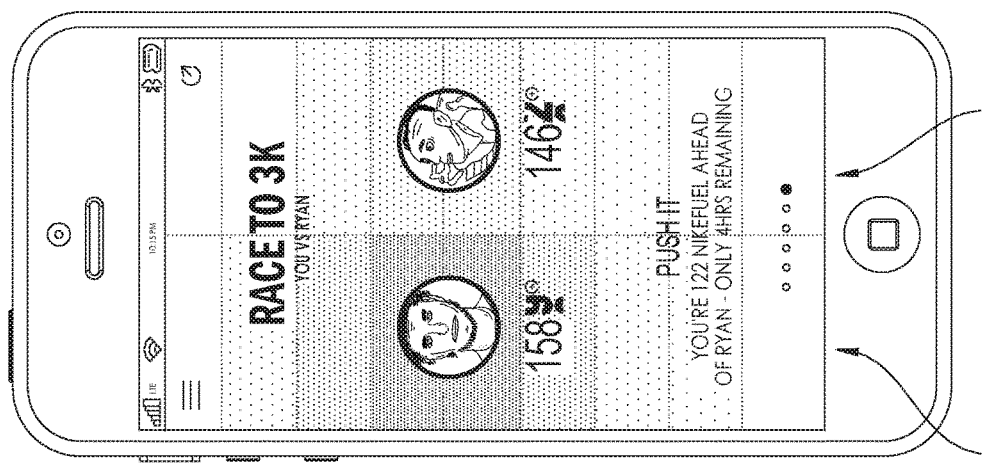
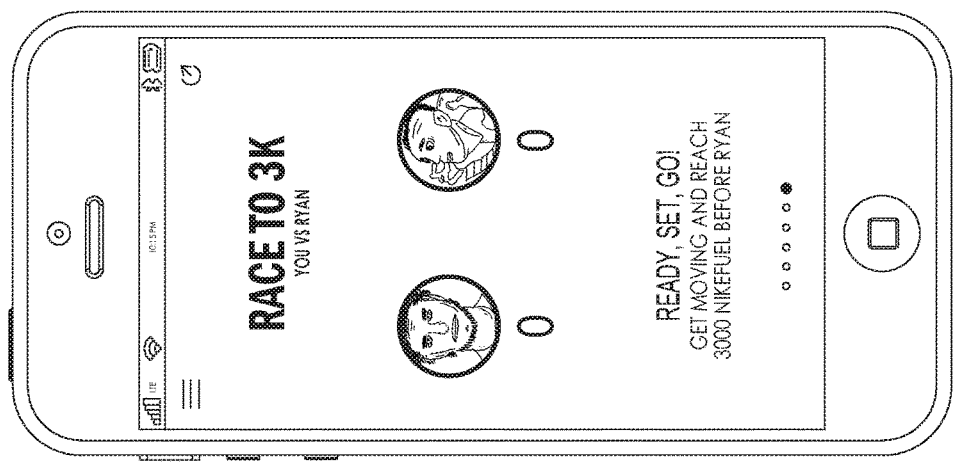
FIG. 14

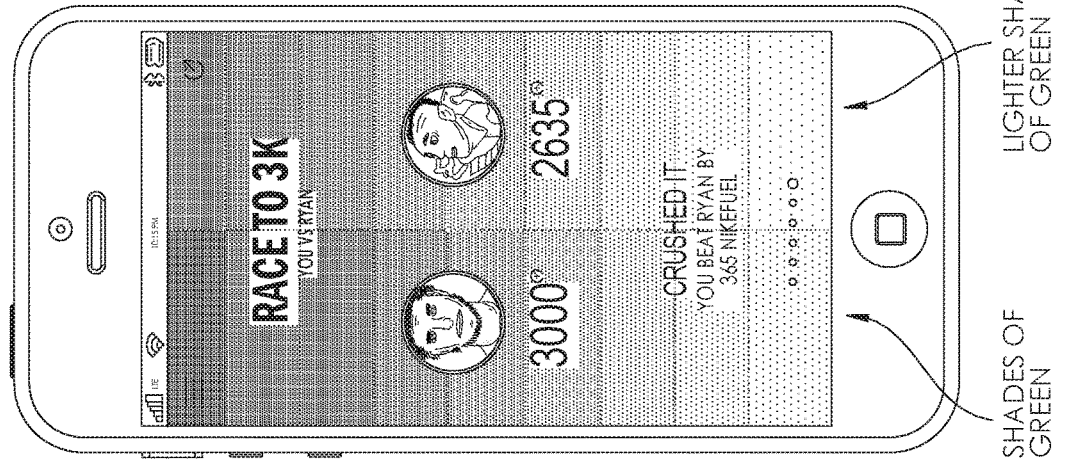
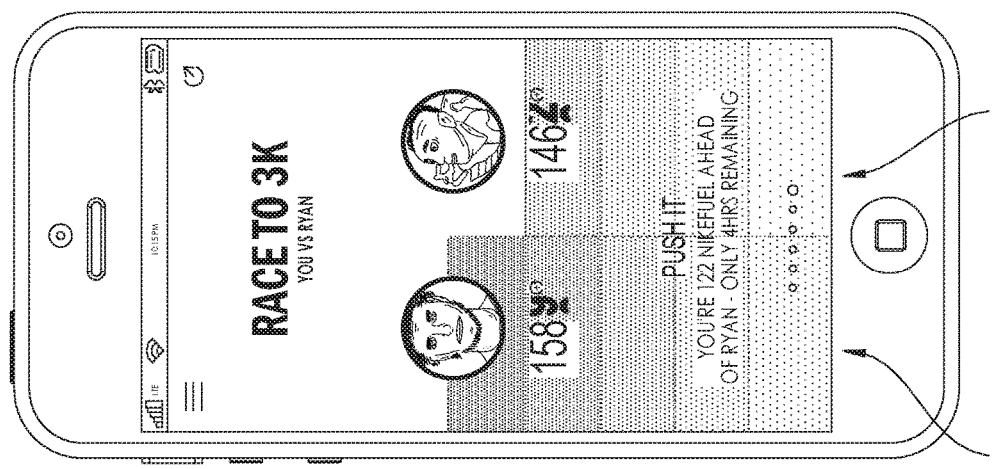
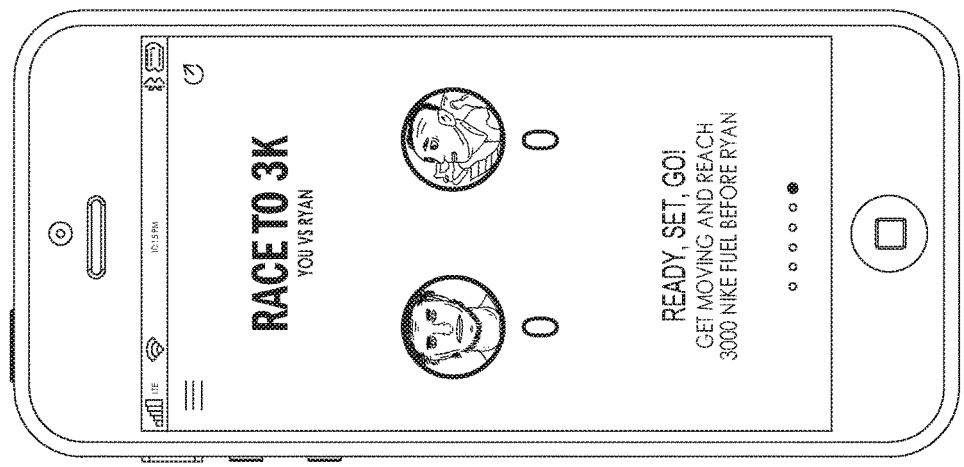
FIG. 15

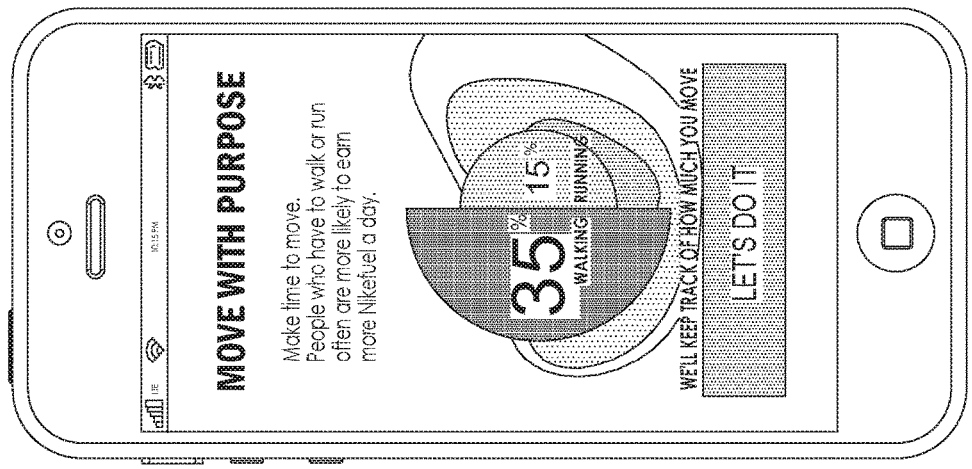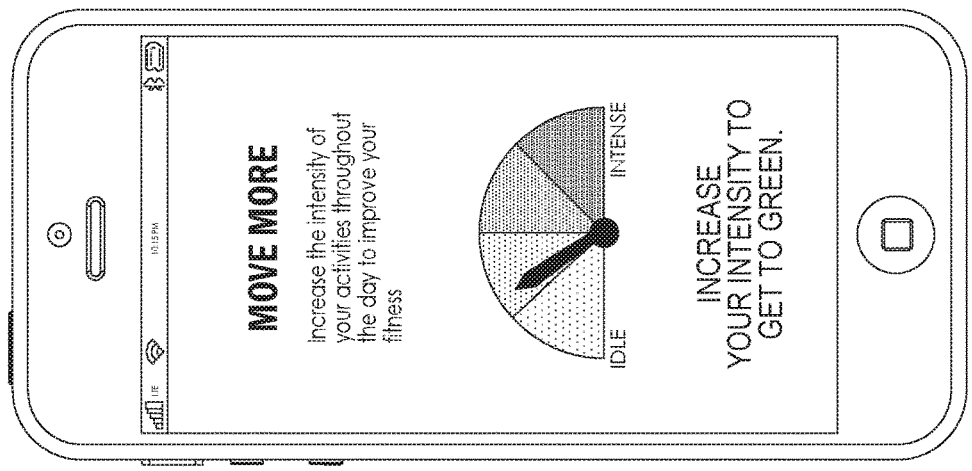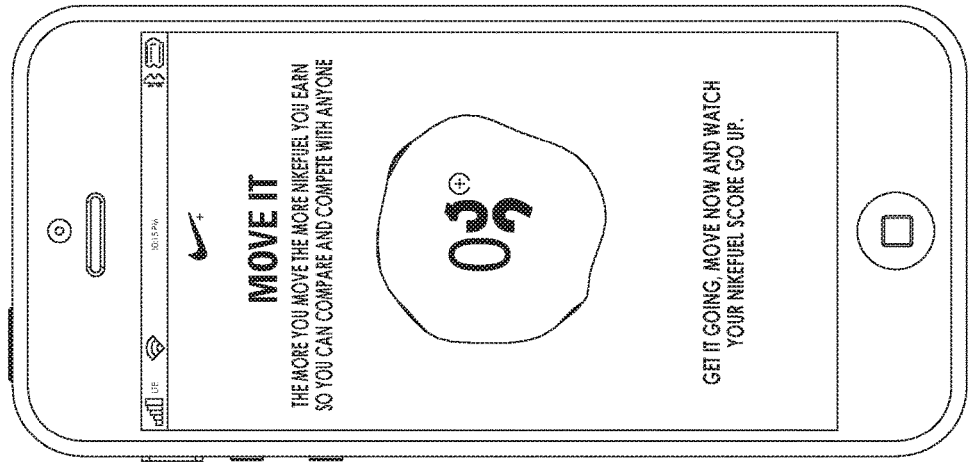
FIG. 16

ENERGY EXPENDITURE DEVICE

CROSS-REFERENCE TO RELATED APPLICATIONS

The present application claims the benefit of and priority to U.S. Patent Application No. 61/869,499, filed Aug. 23, 2013, entitled "Energy Expenditure Device," which is incorporated herein in its entirety.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure relate to calculating energy expenditure values. In certain embodiments, energy expenditure points may be calculated. One or more devices may use an accelerometer and/or other sensors to monitor activity of a user. Under certain implementations, a user may earn energy expenditure points for different activities.

In some embodiments, the present invention can be partially or wholly implemented on a computer-readable medium, for example, by storing computer-executable instructions or modules, or by utilizing computer-readable data structures.

Of course, the methods and systems of the above-referenced embodiments may also include other additional elements, steps, computer-executable instructions, or computer-readable data structures.

The details of these and other embodiments of the present invention are set forth in the accompanying drawings and the description below. Other features and advantages of the invention will be apparent from the description and drawings, and from the claims.

BRIEF DESCRIPTION OF THE DRAWINGS

FIGS. 7-20 show various user interface screens for an embodiment of the invention.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
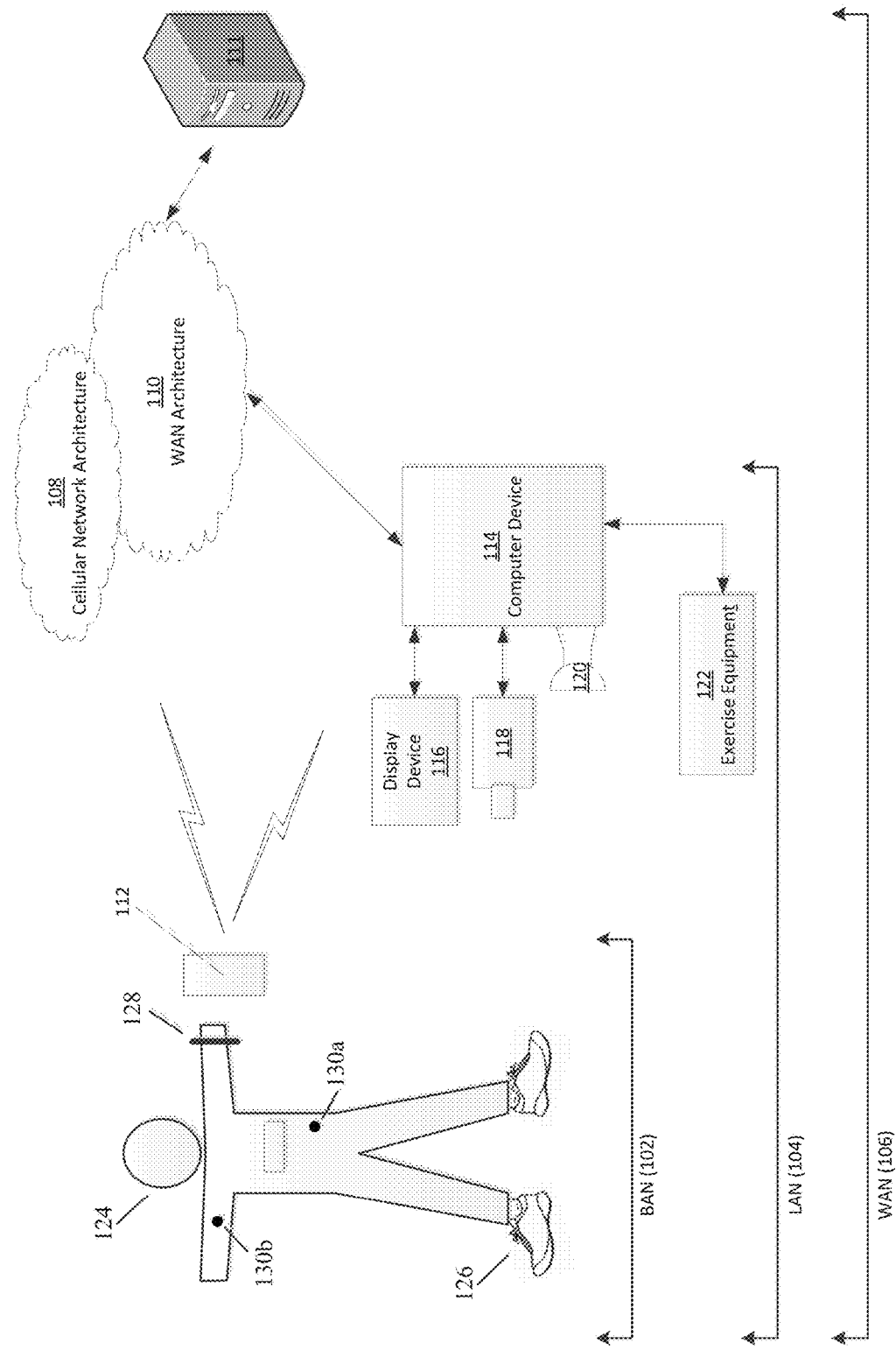
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
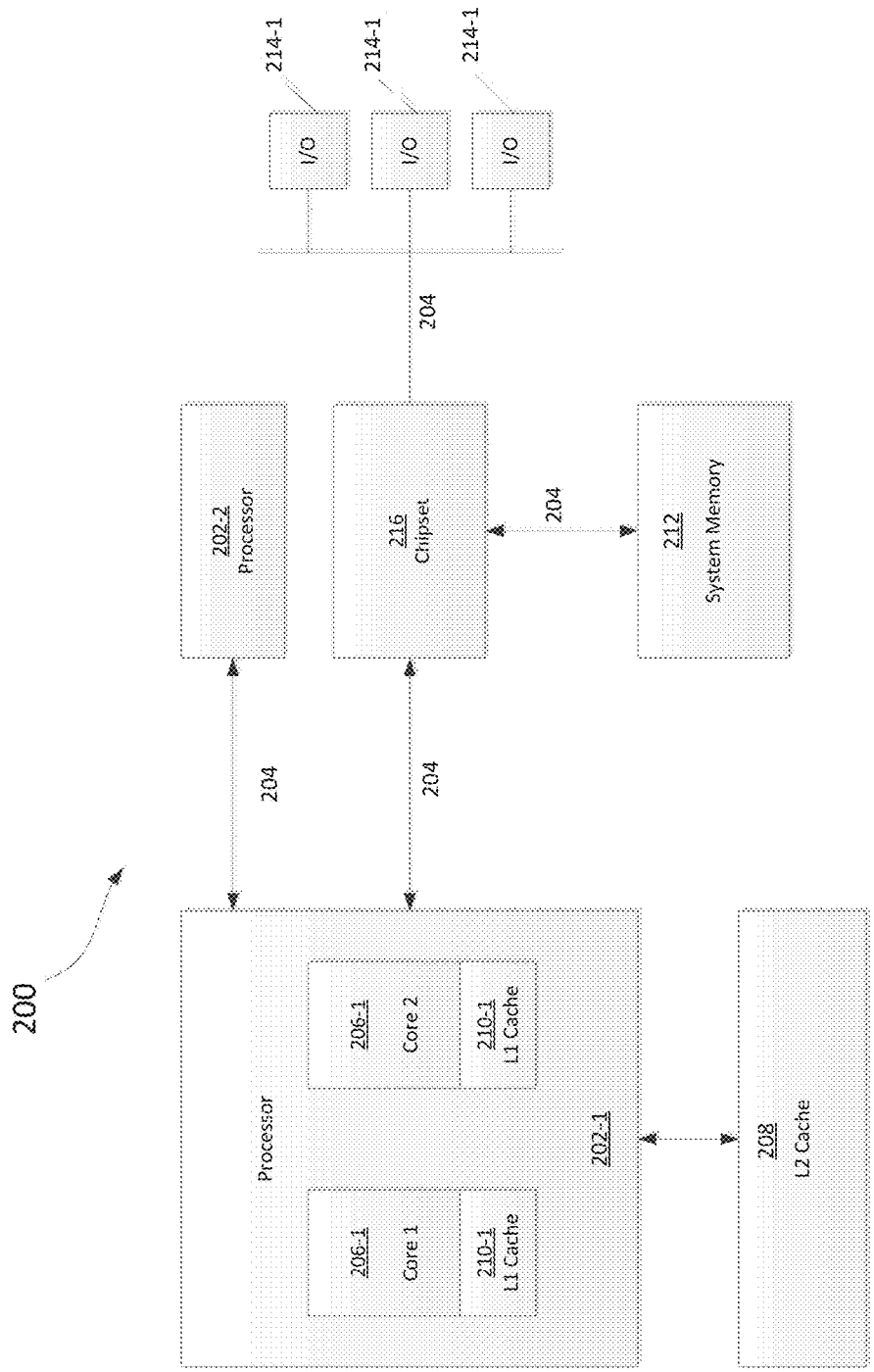
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
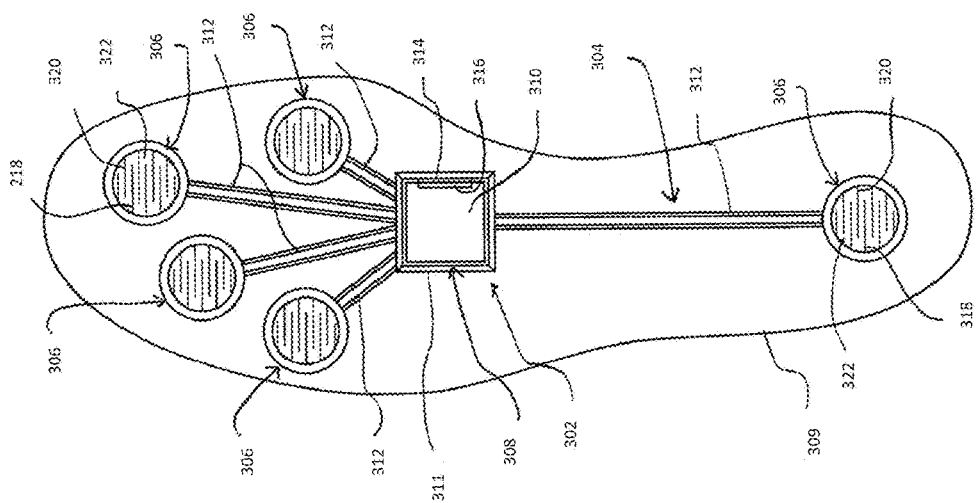
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
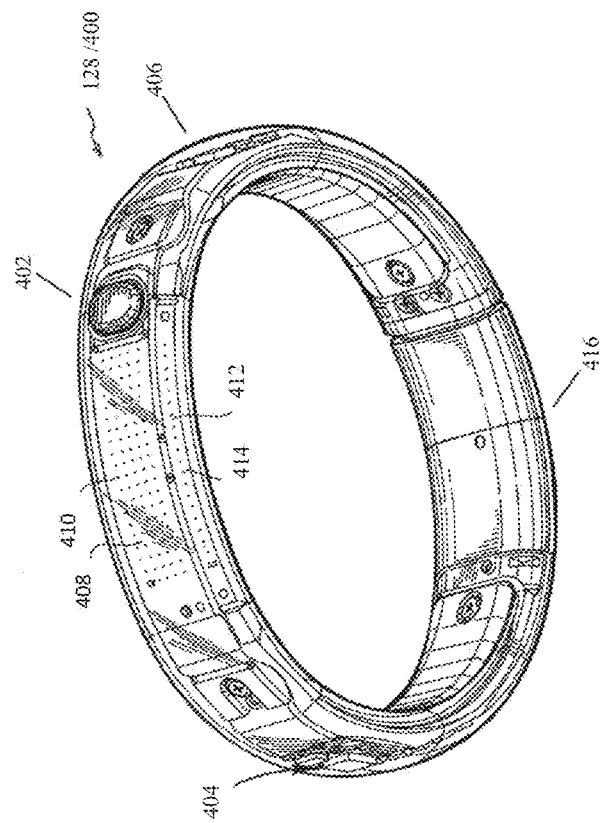
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
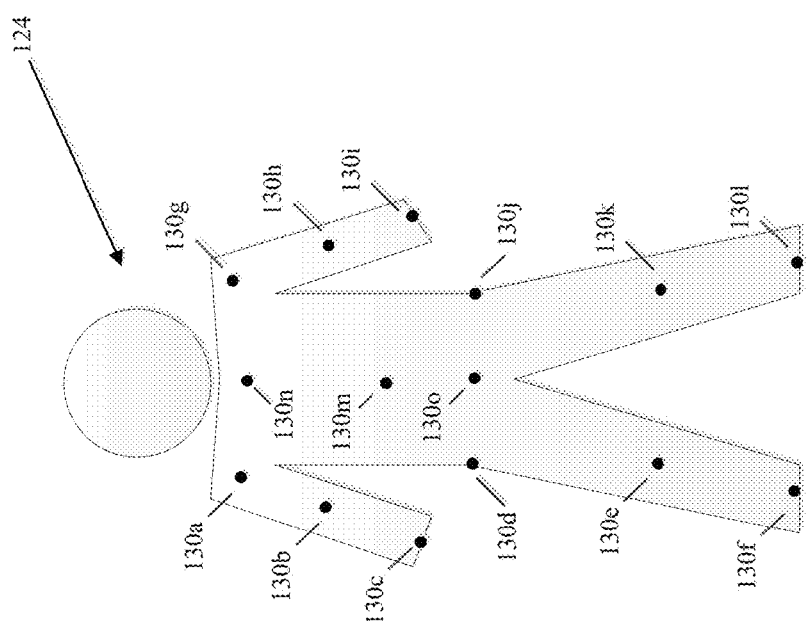
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

II. Energy Expenditure Point Calculations

Figure 6:
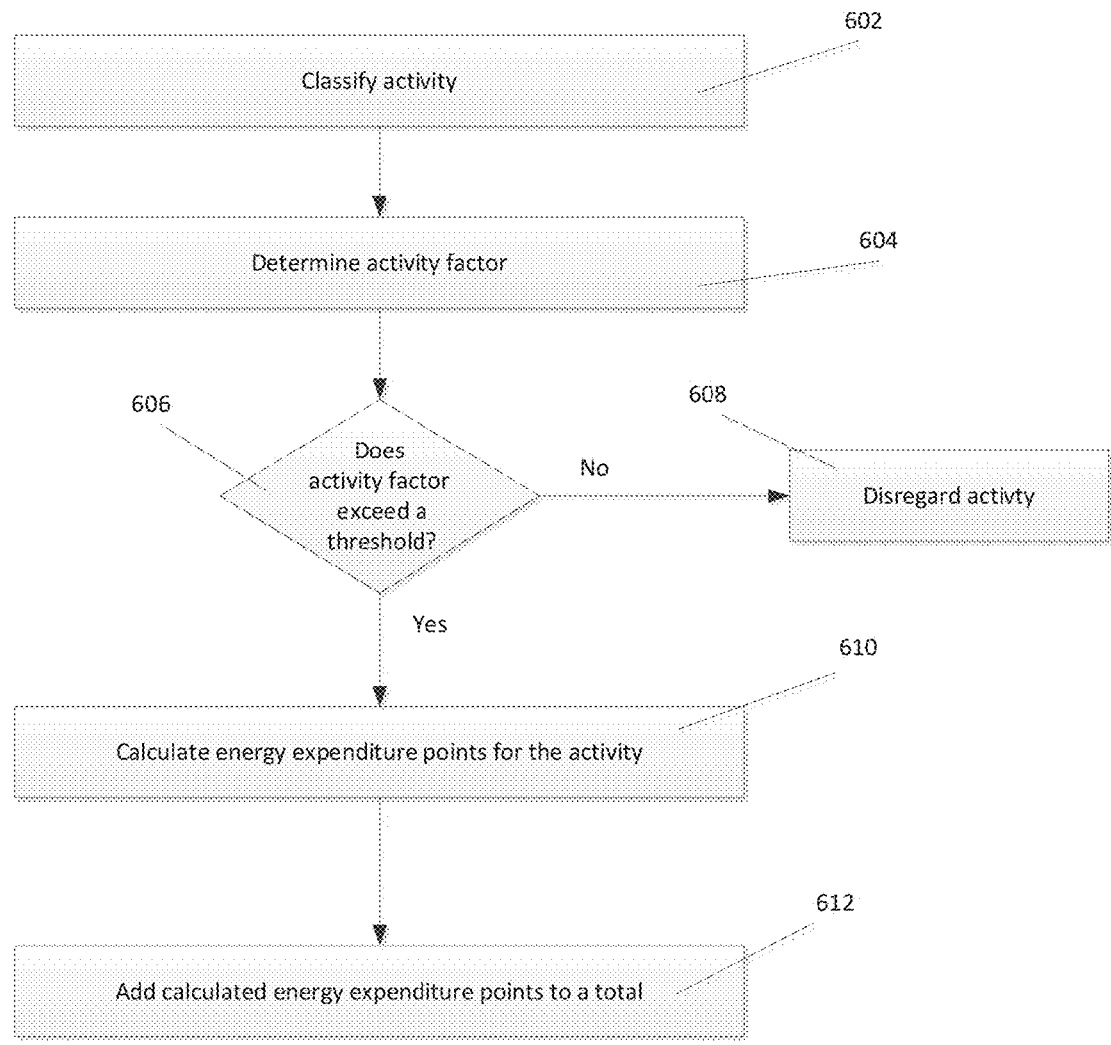
FIG. 6 illustrates a method for calculating energy expenditure values, such as points, in accordance with an embodiment of the invention.

FIG. 6 illustrates a method for calculating energy expenditure values, such as points, in accordance with an embodiment of the invention. Certain embodiments may classify physical motions of a user. For example, at illustrative step 602, one or more activities may be classified. A system may process data received from one or more of the sensors described above to attempt to classify a user's activity. For example, a system may compare a sensor signal to one or more signal or activity "templates" or "signatures" corresponding to selected activities. In certain embodiments, templates may be created by attaching sensors to a user and monitoring signals generated when the user performs various activities. In accordance with certain embodiments, an activity may be associated with an activity template specific to user 124. In one such embodiment, user 124 may be assigned a default template for a specific activity unless a specific template has been assigned to that activity. Thus, user 124 may create or receive (but is not required to create or receive) an activity template that may be more accurate than a default template because the template is more specific to the user and/or the activity. User 124 may have the option to create templates for one or more predefined or undefined activities. A specific or otherwise new template might be shared among the community of users. Shared templates may be based on a variety of different sensors. In some embodiments templates may be refined or adjusted for use with different sensors. For example, a template that was created for use with a shoe based sensor may be refined for use with a wrist worn sensor.

An activity template may also be used to identify motions or actions that a user may perform while performing a particular type of activity. For example, an action may correspond to a group of one or more events, such as detecting that a user has taken a step to the right followed by a step to the left or detecting that a user has jumped while flicking his or her wrist. Accordingly, different sets of one or more actions may define an activity template, and different sets of one or more activity templates may be defined for different types of activities. For example, a first set of activity templates defined for basketball may include dribbling, shooting a basketball, boxing out, performing a slam dunk, sprinting and the like. A second set of activity templates defined for soccer may include kicking a ball to make a shot, dribbling, stealing, heading the ball and the like. Activity templates may correspond to any desired level of granularity. Any number of templates may be defined as needed for a type of activity. In still other examples, as noted above, the templates may be manually selected by a user rather than being selected by the system.

An activity template may be created from data obtained from one or more of a plurality of different sensors. For example, a first group of sensors (e.g. sensors 126 and 128) may be utilized in the formation or refinement of a first activity template; however, a second group of sensors (e.g., sensors 138 and a sensor included in portable electronic device 112) may be utilized in the formation or refinement of a second activity template. In yet further embodiments, a third group of sensors, may be utilized in the creation of the first activity template for a second user (e.g., not user 124) than utilized for the formation of the same activity template as user 124. Thus, in accordance with certain embodiments, there is no requirement that data from a specific sensor be received for either: 1) the same activity template for different users; and/or 2) different activity templates for the same user.

In one embodiment, a wrist mounted accelerometer, which may be a multi-axis accelerometer, may be attached to a user and signal templates based on the accelerometer output when the user runs, walks, etc. may be created. The templates may be functions of the sensor(s) used and/or the locations of the sensor(s). In some embodiments, a single signal (or value) is created by combining multiple signals (or values). For example, three outputs of a three axis accelerometer may be summed or otherwise combined to create one or more signals. Example step 602 may include comparing a signal, multiple signals or a combination of signals to one or more templates. In some embodiments, a best match approach may be implemented in which every activity is attempted to be classified. In other embodiments, if a signal, multiple signals or combination of signals does not sufficiently match a template, the activity may remain unclassified. Some embodiments may utilize only templates for running and walking and a best first approach is used to determine whether the user is running or walking.

Activity classification may be performed by identifying various events and actions represented within the signals and data received from any number and type of sensors. Accordingly, activity tracking and monitoring may include comparing signals and/or sensor data to one or more templates and determining whether one or more expected or known actions has been performed by a user and metrics associated with those actions. In one example, actions may correspond to a series of one or more low-level or granular events and may be detected using predefined activity templates. For example, using activity templates, computer 102 may automatically detect when a user has performed a particular activity or a particular motion expected during that activity. If a user is playing basketball, for instance, detecting that the user has jumped while flicking his or her wrist may indicate that the user has taken a shot. In another example, detecting that a user has moved both feet outward while jumping followed by moving both feet inward while jumping may register as a user performing one repetition of a jumping jack exercise. As noted above, a variety of other activity templates may be defined as desired to identify particular types of activities, actions or movements.

After at least one of user's 124 activity is classified, step 604 may be implemented to determine a corresponding activity factor. An activity factor may correspond to brisk running, running at a moderate pace, walking slowly or any other activity. An activity factor for an activity may be related to calories or energy generally required to perform the activity. If an activity was not classified in step 602, a default activity factor may be selected or derived. In some embodiments multiple default activity factors may be utilized. An activity's intensity, duration or other characteristic(s) may be assessed, from which one or more default activity factors may be applied. The plural activity factors may be set via medians/averages, ranges, or other statistical approaches.

Energy expenditure point calculations may be used in connection with games and competitions. Some games and competitions may limit awarding energy expenditure points for activities that have relatively low activity factors. In some embodiments, awarding energy expenditure points for activities that have relatively low activity factors may also be limited all of the time or in other situations. In step 306 it may be determined whether the activity factor exceeds a threshold value. For example, an exemplary threshold value may be 1.0, 2.0 or 3.0. In another embodiment, the threshold value may equal 2.8. Different games and competitions may use other threshold values. When the activity factor does not exceed the threshold, step 608 may be implemented to disregard the corresponding activity and to not use the activity when calculating energy expenditure points.

Another embodiment could have the threshold generally applied, but not when games or competitions are underway, or at least certain games or competitions. The games or competitions may be based on all points, and may not depend on whether a threshold has been met. In another embodiment, a threshold may always apply even to games and competitions. In another embodiment, different thresholds may apply by activity, game and/or competition, e.g., one for running briskly, one for running, one for walking, one for another activity, and a default.

In various embodiments of the invention, activity factors are used to calculate energy expenditure points. After at least one of user's 124 activity is classified, in step 610 energy expenditure points may be calculated. The use of energy expenditure points ("EEPs") allows for comparison of activity levels and may promote collaboration among users, normalize for competition among users of different capabilities, and otherwise encourage activity. In one embodiment, energy expenditure points are calculated as follows:

$$EEPs = AF * duration \qquad \text{(equation 1)}$$

Wherein:
EEPs=energy expenditure points
AF=activity factor determined in step 604
duration=duration of the activity classified in step 602

Step 610 may be performed at a device that includes sensors that monitor activity and/or at another device that includes a processor, such as portable electronic device 112 or server (see, e.g., server 111). In alternative embodiments, equation 1 may be modified to include other factors, a scalar and/or a different combination of terms.

In some embodiments, equation 1 may be modified to include a scalar that is multiplied by the activity factor and duration. The scalar may be selected so that typical energy expenditure points fall within a desired range of points. The range of points may be desired and/or adjusted for various games or competitions. The scalar may also represent an intensity of the activity. For example, a first scalar may correspond to brisk running and a second scalar may correspond to running at a moderate pace. In alternative embodiments additional activity templates and activity factors may be used and may correspond to the various intensities of running, walking, or another activity.

Variations of equation 1 may be used in other embodiments of the invention. In some embodiments, users may select an equation and/or one or more variables, such as for example, a scalar. Equations may be selected for different games and competitions. In one example, a group may set handicaps among the players based on fitness, so that the most fit players generate EEPs only if they do a common activity or set of activities for longer period(s) of time. A group of users participating in an energy expenditure point competition may agree on a particular equation or method before beginning the competition. In some embodiments of the invention, a user may participate in multiple competitions and earn different points for the same activity because of different calculation methods. For example, a user may be participating in two competitions that have unique calculation methods. The user may earn two different point totals for the two different games and a third point total for their overall energy expenditure. Some point totals may be maintained separate from an overall point total.

Alternative embodiments of the invention may use alternative or additional equations for calculating point values and/or other quantities. The equations may include derivations of measured and/or calculated values. Derivations that include time periods may be used to show rates and rates of change. For example, one equation may be used to determine a rate of accumulating activity points or energy expenditure points. Another equation may be used to determine a quantity of activity points or energy expenditure points accumulated over a predetermined time period.

Some equations may use variables other than time. For example, some equations may be used to calculate a value as a function of activity points or energy expenditure points and steps. Calculating values that are functions of activity points or energy expenditure points and other variables may be used to compare the efficiencies of various activities. For example, an equation may be used to determine that taking steps at a faster pace may result in activity points or energy expenditure points accumulating at a faster per step pace. Another exemplary equation may determine activity points or energy expenditure points per a predetermined distance or a unit of distance, such as a meter, a kilometer, a half-mile, a mile, etc.

Some equations may be used to calculate first and/or second derivatives of measured or calculated values to show rates and rates of change. For example, an equation may be used to calculate or estimate a rate of accumulation of activity points or energy expenditure points at a given time. In some embodiments an instantaneous rate of accumulation of activity points or energy expenditure points is displayed to a user via display 235 or a display that is part of a mobile device.

After the energy expenditure points are calculated, the calculated points may be combined, such as by being added, to a total in step 612. The total may allow user 124 (and/or selected individuals or groups approved by user 124) to see how many points are earned over various periods of time, such as days, weeks and months. Totals may also be calculated for multiple time periods. For example, a user may receive totals for periods that include 24 hours, one week, one month and one year. In some embodiments users may select other time periods and/or deselect time periods. A user may track multiple time periods concurrently and track points awarded since the beginning of use of a device or start of a program. The total for any giving time period may represent points earned for several activities. For example, in a day a user may receive points for walking, jogging and sprinting during different time periods. As mentioned above, the points earned for each activity may be a function of a corresponding activity factor.

Exemplary Embodiments

FIGS. 7-20 show various user interface screens for an embodiment of the invention. The user interface screens may be displayed on portable electronic device 112. Portable electronic device 112 may include one or more sensors configured to detect movement. Exemplary sensors include accelerometers, gyroscopes, location-determining components such as GPS receivers and altimeters. In the exemplary embodiment illustrated in FIGS. 7-12, movement is detected with one or more sensors of portable electronic device 112 and a processor within portable electronic device 112 may be programmed with computer-executable instructions to receive movement data, calculate energy expenditure points and rates of energy expenditure points and generate the illustrated user interface screens. In the example shown, energy expenditure points are in the form of Nike Fuel points.

FIG. 7 shows a user interface screen at 3 different times. Total energy expenditure points for a day or other time period are shown in regions 702, 704 and 706. As shown in FIG. 7, a background color of the user interface may correspond to a current intensity of obtaining energy expenditure points. For example, a red background may correspond to a low intensity, a yellow background may correspond to a medium intensity and a green background may correspond to a high intensity. Intensity levels may be determined by comparing energy expenditure points earned during a time period, such as a minute, five minutes, an hour, etc., to various threshold values.

As shown in FIG. 7, the user interface may display textual messages for further fitness motivation based on an athlete's current and/or past athletic performances. For example, if the total energy expenditure points for a first time period (e.g., 8 AM to 10 AM, a day, a week, etc.) is less than a predetermined threshold, the user interface may display in region 708 a notification that the user is below the threshold and/or some other motivational/encouraging message, such as "Need a Push." "Don't slow down! Almost there," and the like. In one example, the predetermined threshold value may correspond to the total energy expenditure points previously obtained during a second time period. The second time period may correspond to a similar time duration as the first time period. For example, region 708 of the user interface displays a message indicating that the user's current total energy expenditure points is 133 points behind the total energy expenditure points obtained by the user over the same time duration from the previous day. In addition or as an alternative to textual messages, the device may have speech generation hardware, software and/or firmware to produce speech based on text.

As discussed above, certain embodiments disclosed herein relate to calculating an energy expenditure intensity value. As one example, this value may be determined by quantifying the energy expenditure values for a user for a certain time period. For example, energy expenditure values (or derivatives thereof) over a span of time may be used to determine an energy expenditure intensity value for that span of time. Motion data may be obtained from a plurality of different time periods within the time frame. For example, data from a first sensor (which may be an accelerometer, for example) may be obtained every second or multiple times a second and data from a second sensor (such as a force sensor) may be obtained for the same, different or partially overlapping time periods. For example, data from the second sensor may be collected at ½ the rate of the first sensor. Data collected at these time points may be used to determine energy expenditure values for specific time periods within the time frame. The time frame is not required to be static. For example, the time period may be rolling consecutive duration of time. Yet, in other embodiments, the time frame may be static.

Certain embodiments may determine whether one or more energy expenditure intensity values meet a threshold during the time frame. Further embodiments may permit one or more users to compete which user or groups of users obtained more energy expenditure during one or more periods. In one embodiment, if a first user meets an intensity threshold level for a duration and a second user does not meet the intensity threshold level for that duration, the first user may be deemed a winner of that duration. If both users met the threshold level, then a tie may be declared. In another embodiment, total energy expenditure over a larger period of time that includes the duration(s) in which both users met the threshold level) may be used to determine a winner. In yet other embodiments, whichever user obtained a higher intensity level during the duration or the larger time period of time may be used to determine a winner. Certain embodiments may not utilize data from other actual users. In certain implementations, a virtual artificial intelligence ("AI") user may be utilized.

Further embodiments may not utilize data from other users, virtual or real, but rather, a user's performance, such as meeting a goal and/or obtaining a virtual reward, may be based solely on whether they achieve a set threshold, regardless of what other user's data indicates and/or if there is not any other user data for comparison. In this regard, the games, competitions and/or group activities described herein, may be "won" or at least competed in by a single user. For example, a user can "win the day" by obtaining a threshold quantity of hours or time frames in which they met a threshold intensity level. As another example, a user can "win the hour" by obtaining a threshold quantity of minutes or time frames in which they met a threshold intensity level. Thus, all disclosure herein relating to comparing a first user's data to a second user's data also is intended to disclose comparing a first user's data to electronically stored data that may not have been collected from actual activity data of another user.

In one embodiment, it may be quantified how many times a user meets a threshold intensity level for a time frame (such as an hour or a day). Systems and methods may be implemented to quantify the number of times a plurality of users each meet a threshold within a set time, such as within with a day. Certain methods may be configured to permit users to compete for instances of meeting a threshold level of intensity in a day or other length of time. As one exemplary embodiment, it may be determined whether any of a plurality of users obtained an intensity threshold level in a set amount of time. If a user meets the threshold level for any set duration, which may be measured by ensuring they have a plurality of consecutive expenditure values, then they may get credit for a longer period of time. The quantity of threshold intensity levels meet for the specified durations may be quantified and one or more users may be ranked or otherwise compared. For example, a user may "win the day" if that user met more threshold levels than another user or above a threshold quantity. As discussed above, one or more tie-breakers may be used. Further, as discussed throughout this disclosure, certain criterion may be used to determine whether sensor data is considered and/or how it may be processed. Further, although an exemplary threshold level was discussed, those skilled in the art will appreciate that multiple threshold levels may be used. In one embodiment, a higher threshold intensity level may be weighted in ranking and/or determining a winner.

FIG. 8 shows user interface screens that include curves 802 and 804 that indicate energy expenditure point level intensity over time. As shown in the figure, as intensity increases, curves 802 and 804 move toward the top of the screen and may transition in color from red (low intensity) to yellow (medium intensity) to green (high intensity). In one embodiment, the user interface screens may include an icon or other symbol indicating the total energy expenditure points earned during a given period of time. For example, icon 814 indicates that the user earned 479 energy expenditure points over a period of one hour (e.g., between 4:00 PM and 5:00 PM).

Each of the user interface screens may also include an icon or other symbol that indicates when the user has exceeded an intensity threshold for a given period of time. The threshold may require exceeding an energy expenditure point rate for a predetermined period of time. For example, in one embodiment, the threshold may require the user to exceed an energy expenditure point rate for a predetermined number of minutes out of an hour. As shown in FIG. 8, rows 806 and 808 indicate when the user has exceeded an intensity threshold over a given period of time. Additionally or alternatively, in some embodiments, the threshold may require the user to exceed the total energy expenditure points or energy expenditure intensity value earned by a second user during a similar time frame.

Rows 806 and 808 each include a series of circles (e.g., sub-icons) that represent incremental time periods over a particular time frame (e.g., unitary time frame). Each circle may correspond to a particular time period (e.g., 15-minutes, 30-minutes, 1 hour, etc.) within the time frame. For example, row 806 includes thirteen circles and each circle (e.g., sub-icon) represents a one-hour period of time. As such, curve 802 shows energy expenditure point level intensity over a time frame of 13 hours. Rows 806 and 808 also include dark circles, which indicate the particular time periods (e.g., hours) that the user has exceeded the intensity threshold. For example, row 806 includes 3 dark circles representing the three one-hour time periods that the user has exceeded the intensity threshold within the corresponding time frame. Similarly, row 808 includes 7 dark circles representing the seven one-hour time periods that the user has exceeded the intensity threshold within the corresponding time frame.

Text sections 810 and 812 correspond to the number of dark circles, and further indicate whether the user has won a particular time period and/or the total number of time periods won by the user. In some embodiments, as illustrated in FIG. 8, the user interface may provide one or more activity recommendations to the user, such that the user may perform sufficient activity to exceed the intensity threshold for a particular time period. For example, as illustrated in FIG. 8, text section 812 indicates that the user must continue moving (e.g., remain active) for at least an additional 5 minutes in order to win the hour (e.g., exceed the intensity threshold).

As another example, the user interface may display a message to motivate a user to conduct activity if they have not hit a threshold level for a duration of time. Similarly, a notification may be provided to indicate that the user is unlikely to meet a threshold level, such as for a duration of time that includes the current time the user is intended to get the notification. A second reminder, which may be the same or different from the first reminder, could be provided again when less time remains. In some embodiments, the notification may be configured to be generated on a device that comprises at least one sensor that created at least a portion of the user's motion data. In one embodiment, the device may be configured to be worn on an appendage, such as for example, on a user's arm, wrist, or leg. The device may comprise at least one accelerometer for obtaining motion data. In further embodiments, the device may not only generate the notification, but also configured to provide the notification, such as through a display, audio, tactile feedback (e.g., vibrations) and combinations thereof. In other embodiments, the notification may be generated on a first device, such as a computer or portable electronic device and transmitted to a device having at least one of the sensors used to collect the data.

Figure 9:
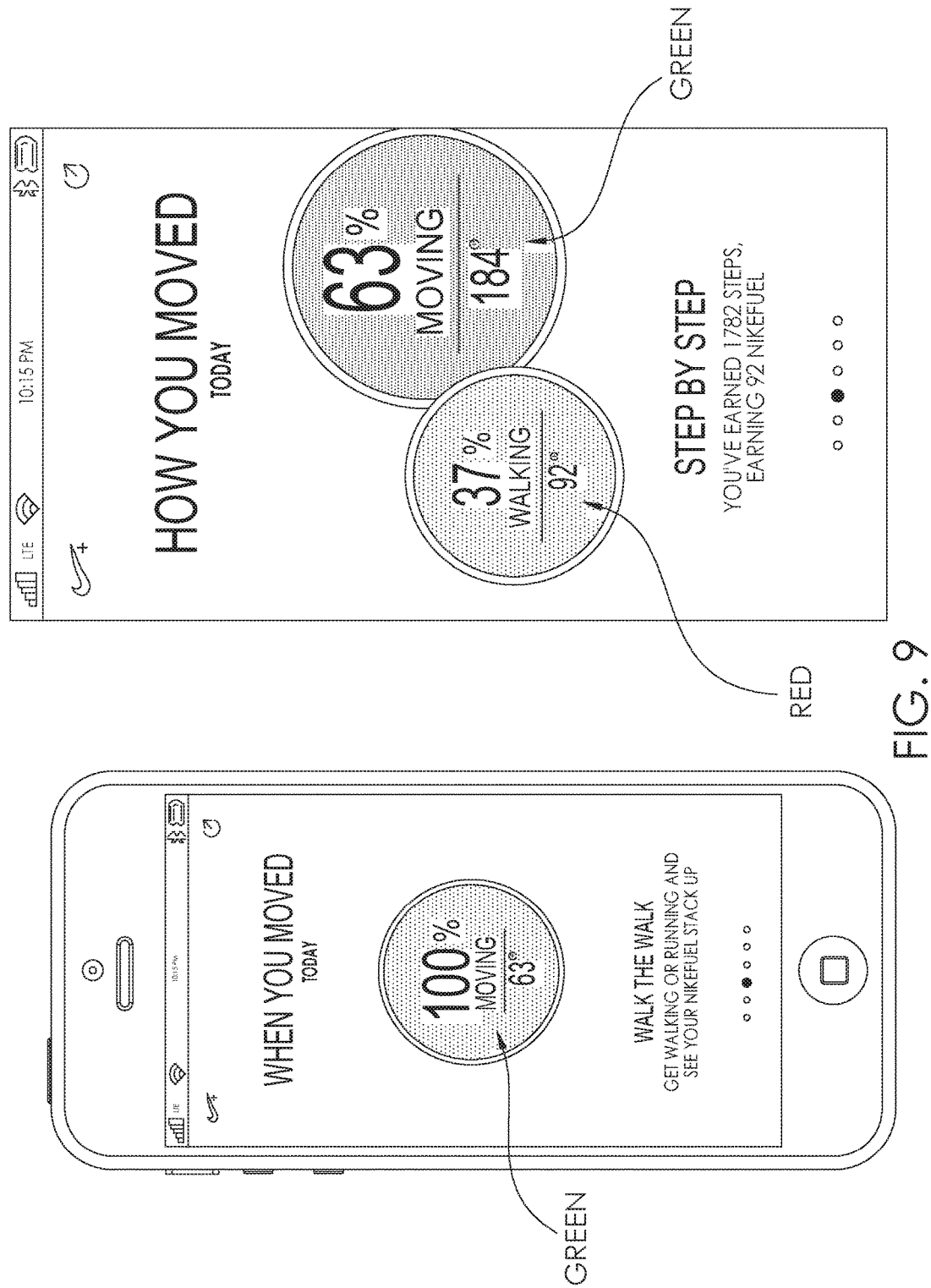
Figure 10:
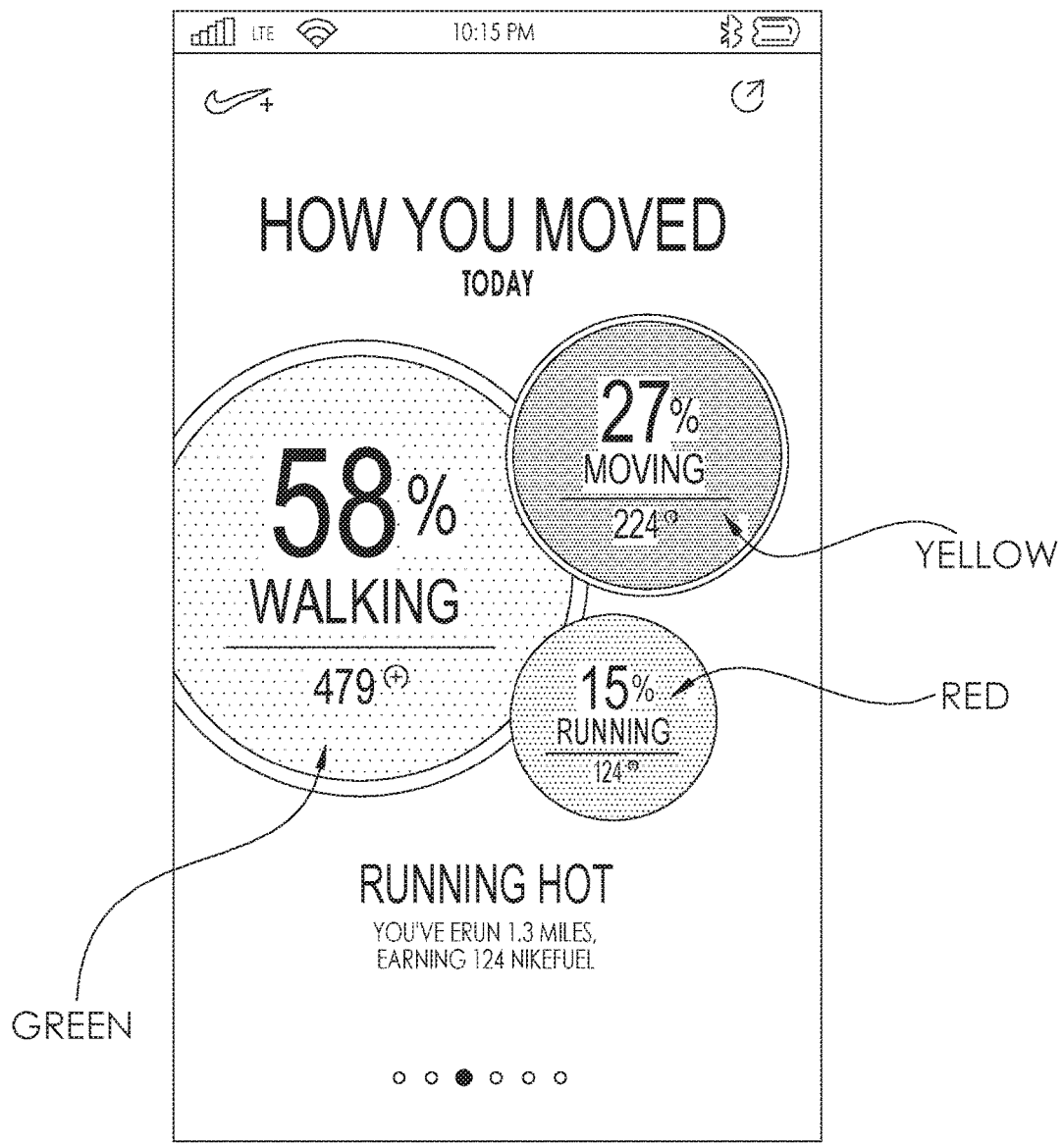

FIGS. 9-10 illustrate user interface screens that may be used to indicate activities, energy expenditure points and energy expenditure intensity values. Activities may include moving, walking, running, and other activities, and may be determined by comparing data received from one or more sensors to activity templates. The user interface my display or show one or more of the various activities performed by a user as an icon or other virtual object. Additionally or alternatively, the user interface may also indicate the total energy expenditure points associated with and/or attributable to a particular activity type. Energy expenditure intensity values may be indicated with colors. For example, a red icon may correspond to a low energy expenditure intensity value, a yellow icon may correspond to a medium energy expenditure intensity value and a green icon may correspond to a high energy expenditure intensity value. Energy expenditure intensity values may also be indicated by size. For example, a small icon may correspond to a low energy expenditure intensity value, a medium-sized icon may correspond to a medium energy expenditure intensity value and a large icon may correspond to a high energy expenditure intensity value.

Figure 11:
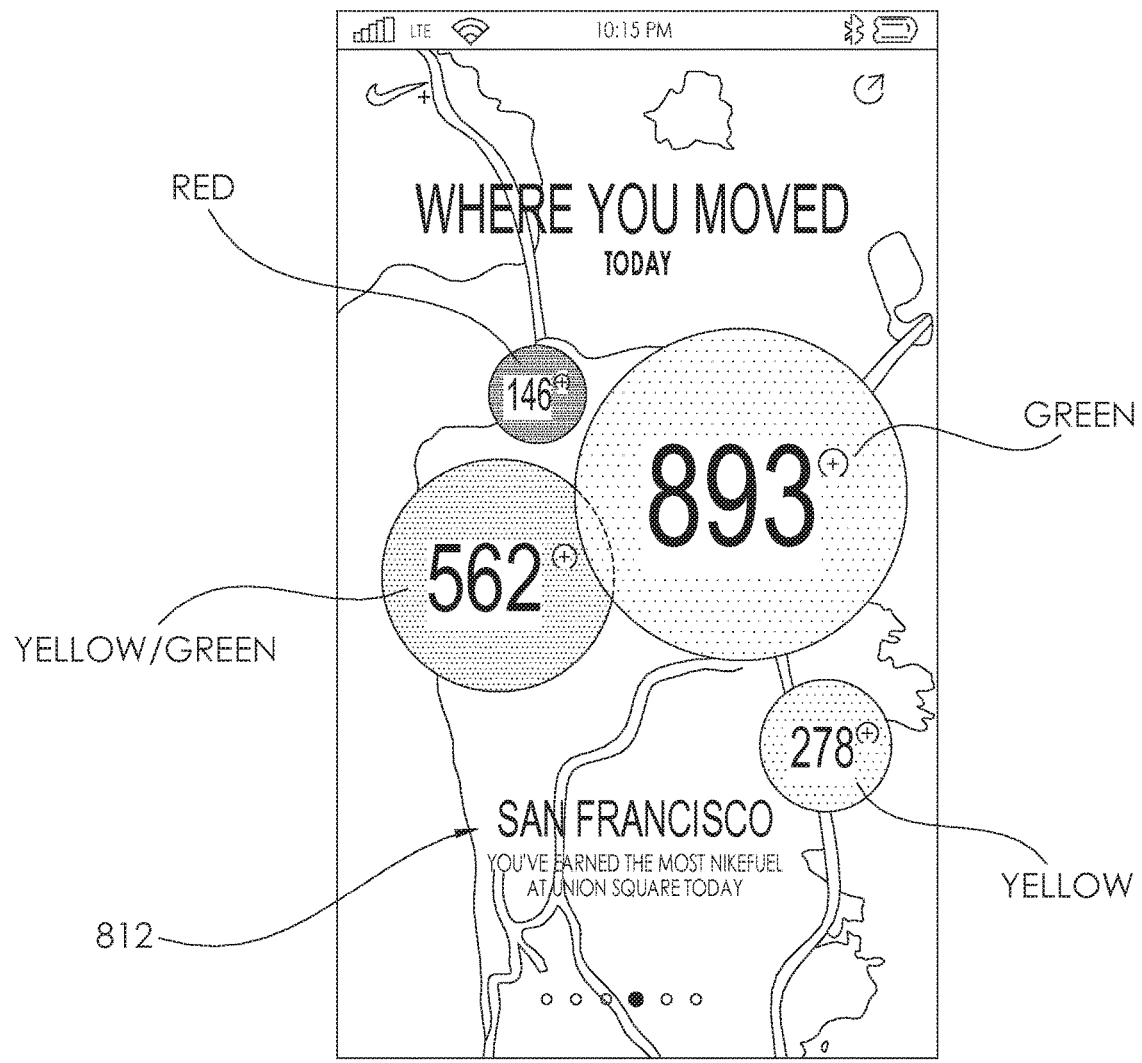

FIG. 11 illustrates a user interface screen that may be used to indicate energy expenditure points, energy expenditure intensity values and geographic locations where the points were earned. Bubbles, icons or other virtual objects may be colored coded to represent energy expenditure intensity values. For example, as depicted in FIG. 11, a red bubble may correspond to a low energy expenditure intensity value, a yellow bubble may correspond to a medium energy expenditure intensity value and a green bubble may correspond to a high energy expenditure intensity value. Additionally or alternatively, the size of the bubbles, icons, or other virtual objects may correspond to the amount of energy expenditure points earned at each location. In other embodiments, the size of the bubbles, icons, or other virtual objects may correspond to expenditure intensity values for each location. For example, as depicted in FIG. 11, a small bubble may correspond to a low energy expenditure intensity value, a medium-sized bubble may correspond to a medium energy expenditure intensity value and a large bubble may correspond to a high energy expenditure intensity value.

In some embodiments, the user interface may display a map associated with one or more geographic areas where the user performed athletic activity. Locational data for the user may be obtained via a GPS sensor associated with the device (e.g., portable electronic device 112). As illustrated in FIG. 11, each bubble, icon, or other virtual object displayed on the user interface may be centered on a particular geographic location where the energy expenditure points were earned. One or more regions of user interface may also display textual messages (e.g., region 812) indicating the geographic region where energy expenditure points were earned by the user. Locational data may be processed to determine and/or identify one or more physical or historical landmarks associated with the particular geographic region where energy expenditure points were earned (e.g., the location where athletic activity was performed by the user). For example, with respect to FIG. 11, the user interface indicates that the user earned 893 energy expenditure points at the Union Square landmark in San Francisco.

Figure 12:
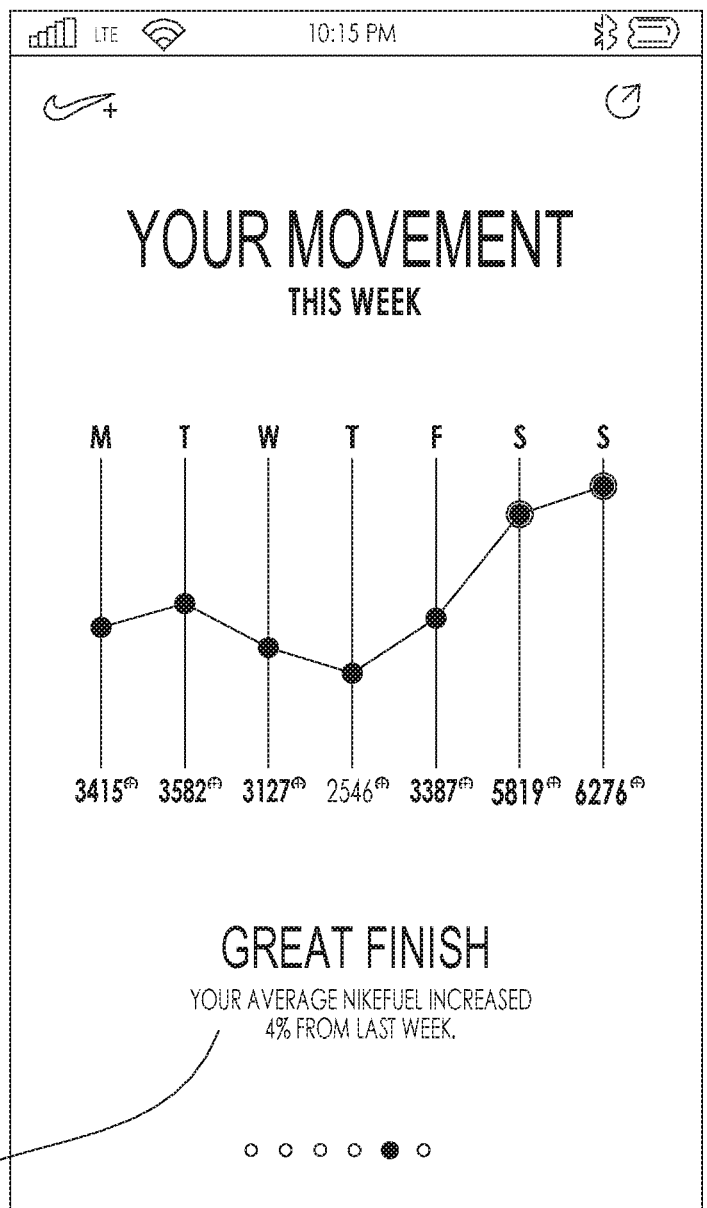

FIG. 12 illustrates a user interface screen that shows energy expenditure points earned during a week. As shown, portable electronic device 112 may be configured to compare weekly point totals and generate a message regarding the comparison. In some embodiments, the user interface screen may include icons, coloring shading or different icon sizes to indicate how energy expenditure points earned on one day compare to energy expenditure points earned on another day, such as the same day during a previous week. For example, as illustrated in FIG. 12, one or more icons may have diminished visibility relative to other icons displayed in the user interface so as to indicate the particular time periods (e.g., days) where a low number of energy expenditure points were earned. The user interface may also display textual messages providing encouragement or motivation based on the user's athletic performance. In some embodiments, the user interface may display athletic metrics associated with a user's athletic activity. For example, the user interface may display the number of miles ran or the number of steps taken by the user during an athletic activity. As another example, the user interface may display athletic metrics comparing a user's current athletic activity with their previous athletic activity. As illustrated in FIG. 12, the user interface indicates at region 1212 that the user's average number of energy expenditure points earned has increased by 4% from the number of energy expenditure points earned by the user during the previous week.

Figure 13:
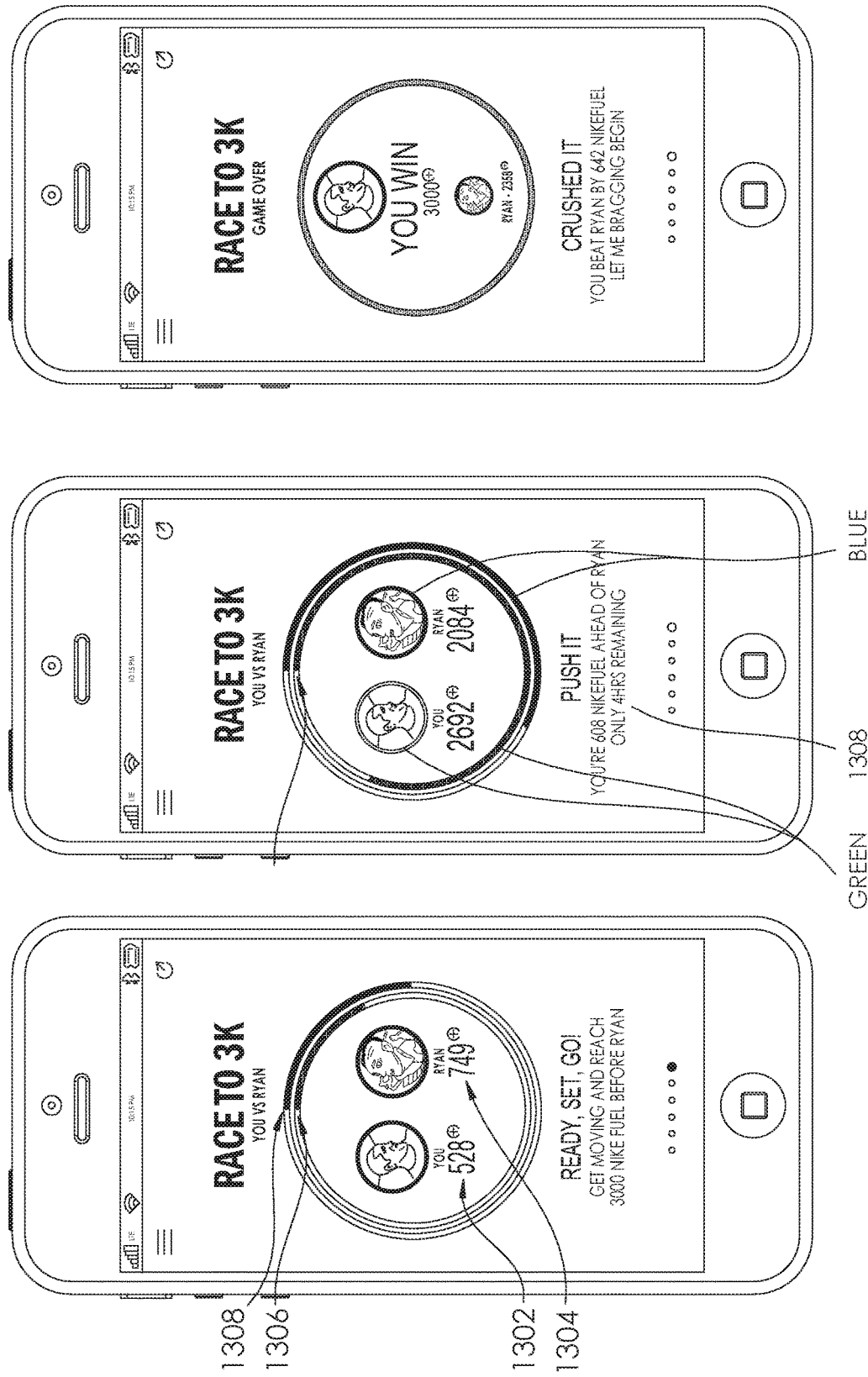

As noted above, in some embodiments, users may challenge each other to earn energy expenditure points. FIG. 13 illustrates user interface screens that may be displayed on portable electronic device 112 during a challenge. Energy expenditure point totals for each person are shown in sections 1302 and 1304. Rings 1306 and 1308 may be used to graphically illustrate the current state of a challenge. Point totals and rings may be color coded to show user associations. For example, point total 1302 may be the same color (e.g., green) as ring 1306, and point total 1304 may be the same color (e.g., blue) as ring 1308. As shown in the figure, as points are earned, a larger portion of each rings is colored or shaded to show user progress toward completing the challenge. The user interface may display textual messages indicating the current status of the challenge. For example, the interface may display the number of energy expenditure points required to complete the challenge, the amount of time remaining to complete the challenge, and other challenge status information.

FIGS. 14-15 illustrate alternative user interface screens that may be used to show that status of a challenge. One skilled in the art will appreciate that challenges with two users are shown for illustration purposes only. Alternative challenges may include 3, 4 or more users. In some embodiments users may select challenge opponents. In other embodiments opponents are selected by one or more portable electronic device 112 or by another computer device, such as server 111. In some embodiments, portable electronic device 112 may visually modify the one or more portions of the background of the user interface to indicate a user's progress toward completing a challenge. As users compete to be the first to earn 3000 energy expenditure points, the background of the user interface associated with each user is visually modified (e.g., shaded, colored, etc.) so as to indicate user progress toward completing the challenge. In other examples, the user interface may be visually modified to identify the user who is winning the challenge, (e.g., closest to completing the challenge goal). As shown in FIGS. 14 and 15, one or more portions or segments of the user interface background may be visually modified to indicate a user's progress toward completing the challenge.

Figure 17:
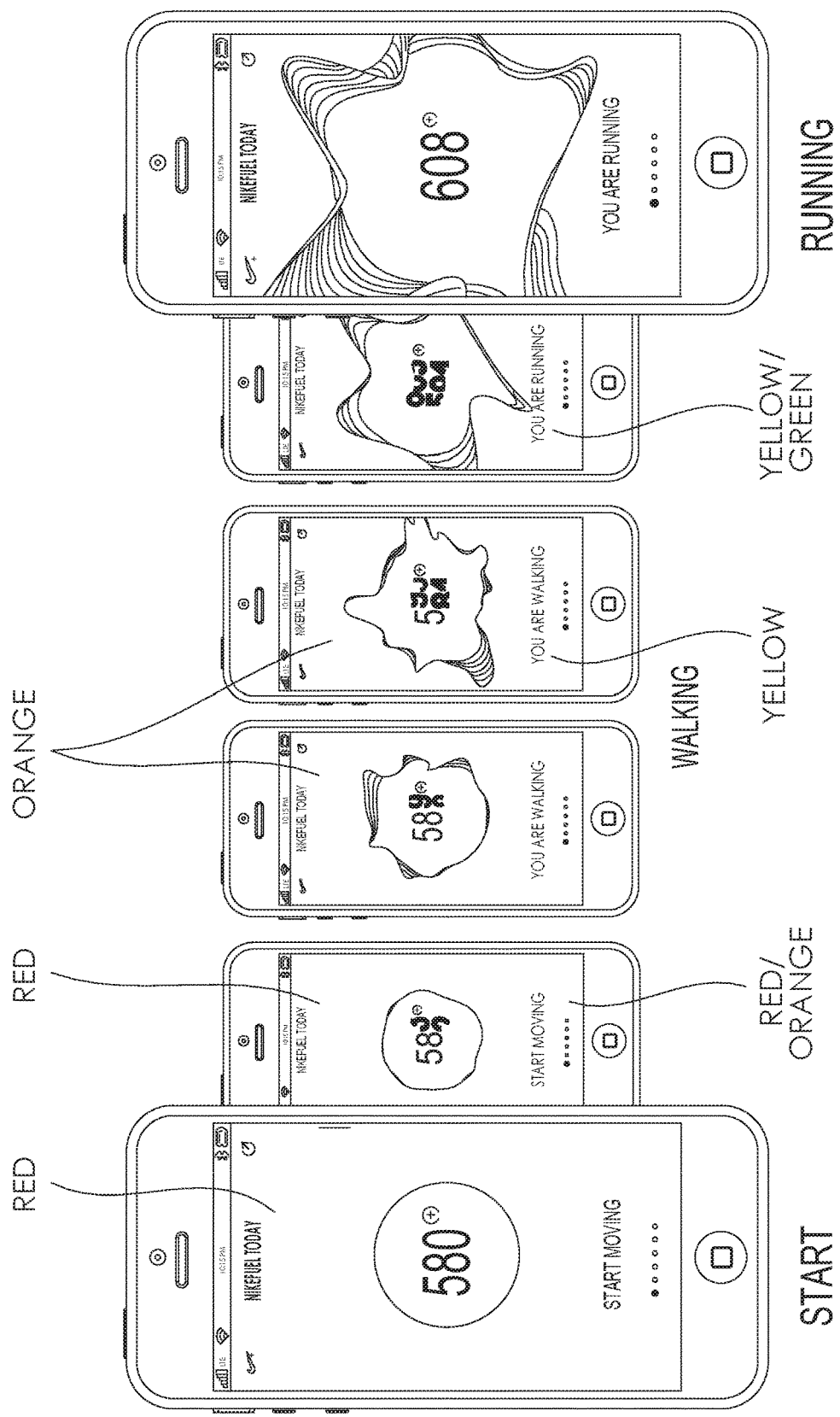

FIG. 16 shows user interface screens that may be used to motivate users and/or provide useful tips and information for earning energy expenditure points. FIG. 17 shows a user interface screen at different times while the user varies energy expenditure intensity values. Initially the user interface background is red to indicate low intensity (e.g., a low level of physical activity, idle movement, etc.). The user interface background transitions from red to orange to yellow as the energy expenditure intensity value increases to a medium level (e.g., walking) As shown, part of the background may be one color (e.g., red) and another part may be another color (e.g., orange) during the transition. Toward the right side of the figure, the background transitions from yellow to green as the energy expenditure intensity value increases to a high level (e.g., running)

Figure 18:
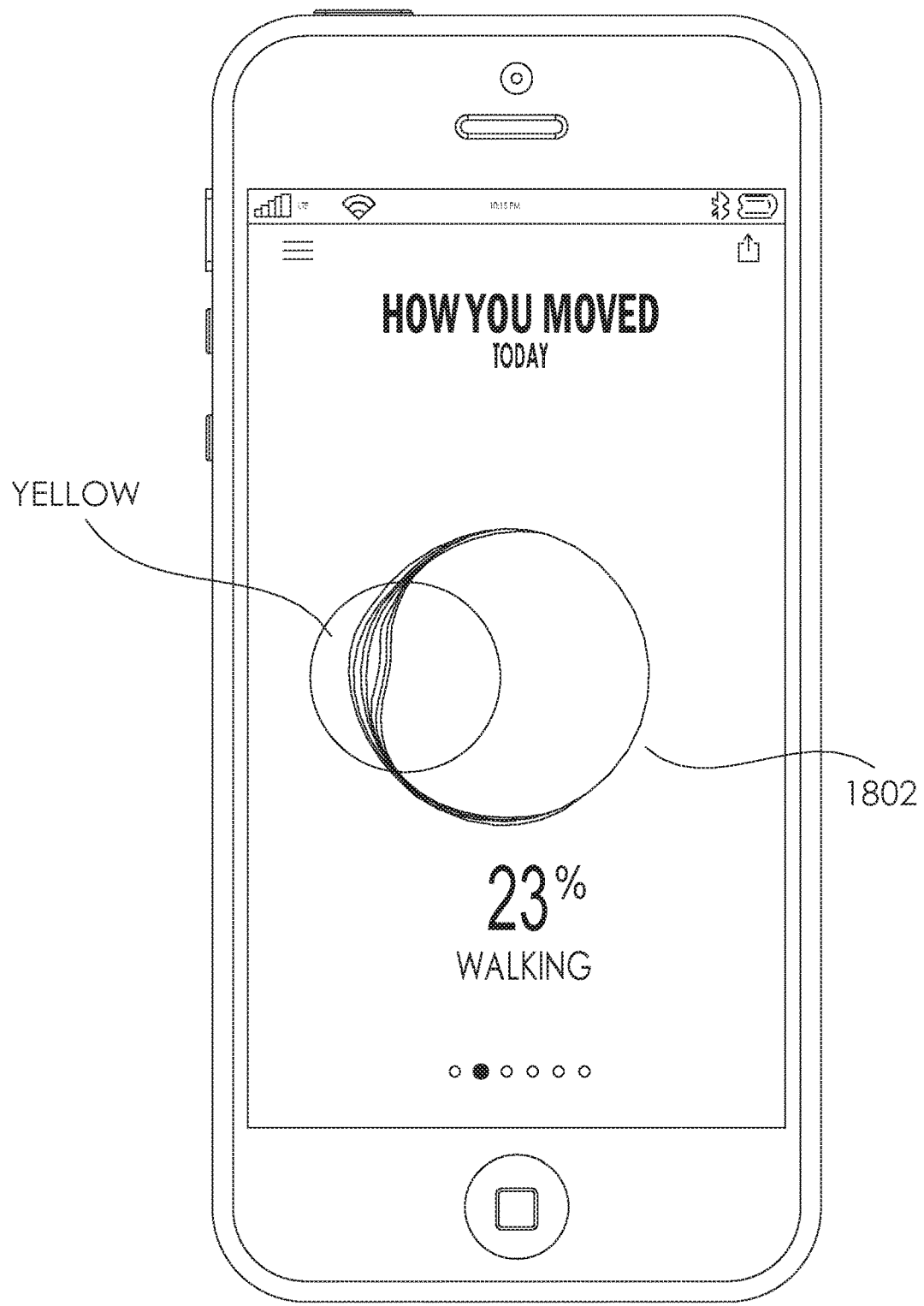

FIG. 18 illustrates a user interface screen that shows activity during the day. Activities and/or intensities may be classified and represented on ring 1802. Intensities and activities may be color coded and one or more segments of ring 1802 may be expanded in appropriate colors to represent the activity or intensity of the user for a time period (e.g., a day). FIG. 18 shows that the user walked 23% of the day and includes an expanded yellow section representing the user's athletic activity. If the user would have instead ran for 33% of the day, the expanded section may be larger and colored green to represent the user's athletic activity and increased energy expenditure intensity.

Figure 19:
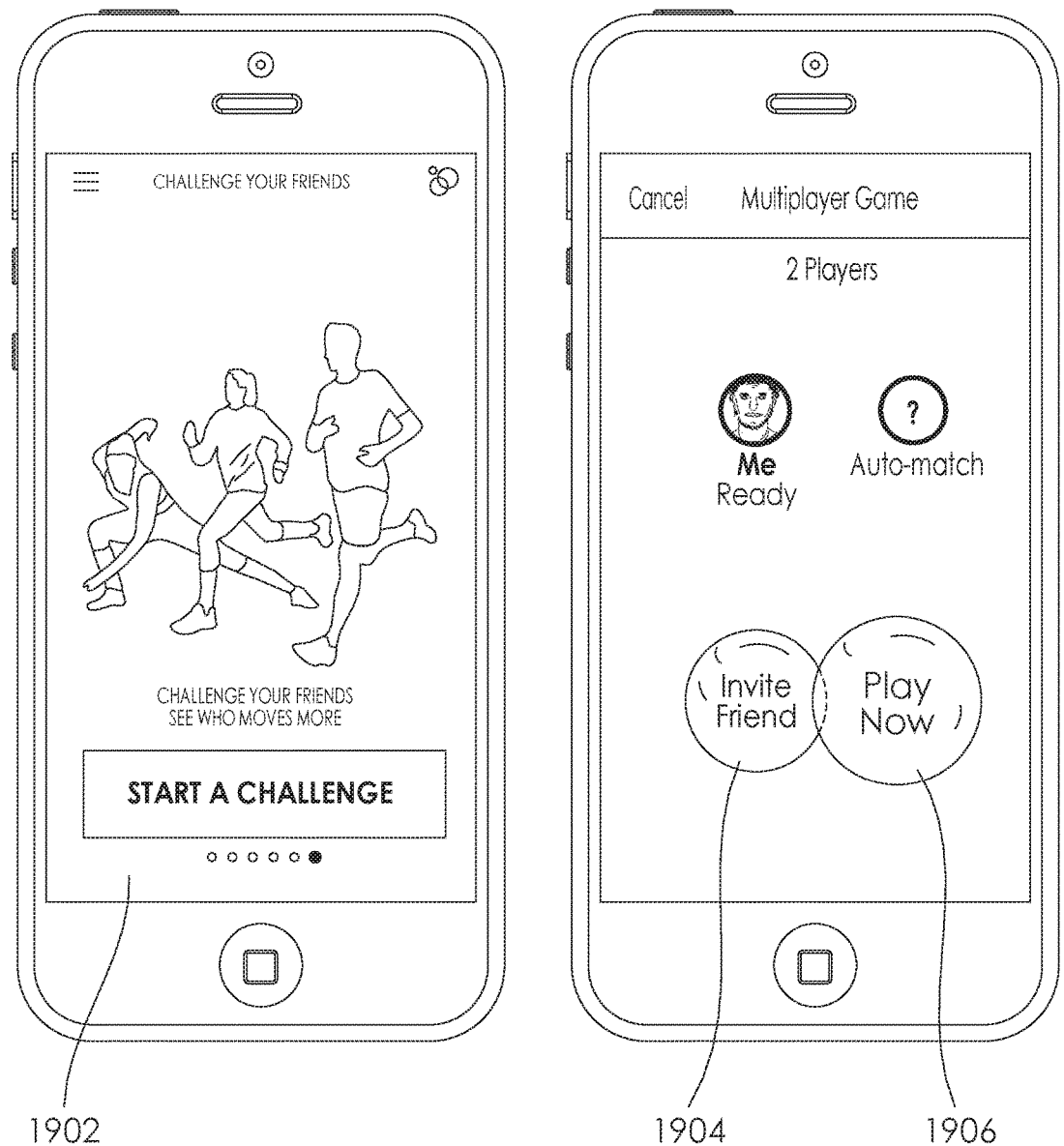

FIG. 19 illustrates user interface screens that may be used to initiate challenges. As discussed above, various examples of the invention may allow a user to "challenge" one or more other users (i.e., athletes employing embodiments of the invention) to a competition regarding athletic activities. With some implementations of the invention, for example, a user may issue a challenge to one or more other athletes by requesting the user interface 1902 shown in FIG. 19. The user may utilize the "Invite Friend" button 1904 to invite one or more other users to participate in the challenge. If an invitee agrees to join the challenge by responding to the invite, then the portable electronic device 112 will be notified that the invitee has agreed to join the challenge. The user interface may display one or more icons indicating the users that have accepted the challenge. After the desired participants have been identified and accepted the invite, the user may initiate the challenge by activating the "Play Now" button 1906.

After the challenge has been initiated, the portable electronic device 112 or some other device, may monitor the collected activity data for each of the participants, and aggregates the relevant data values in the collected activity data. For example, if the challenge is a race to determine who can be the first to run 100 miles, for each participant the portable electronic device 112 will sum the total distance value in each activity data set collected for that participant after the start date. When a participant has a sum of his or her total distance values that matches or exceeds the specified challenge distance (and is the first invitee to do so), then the portable electronic device 112 may identify that participant as the winner of the challenge. In response, the portable electronic device 112 may notify each participant of the winner. The portable electronic device 112 may notify the participants using any desired technique, such as by sending an electronic mail message, by displaying a special-purpose interface, etc. A variety of such notification techniques are well known in the art, and thus will not be discussed in detail.

With various examples of the invention, the portable electronic device 112 may additionally provide updates regarding the status of a participant relative to the other participants. These updates also can be provided using any desired technique, such as by sending an electronic mail message, by displaying a special-purpose interface, etc. For example, the portable electronic device 112 may configure and provide a user interface showing each participant's progress toward the goal of the challenge using, e.g., rings for each participant of the type previously described with regard to monitoring individual levels of athletic activity.

Figure 20:
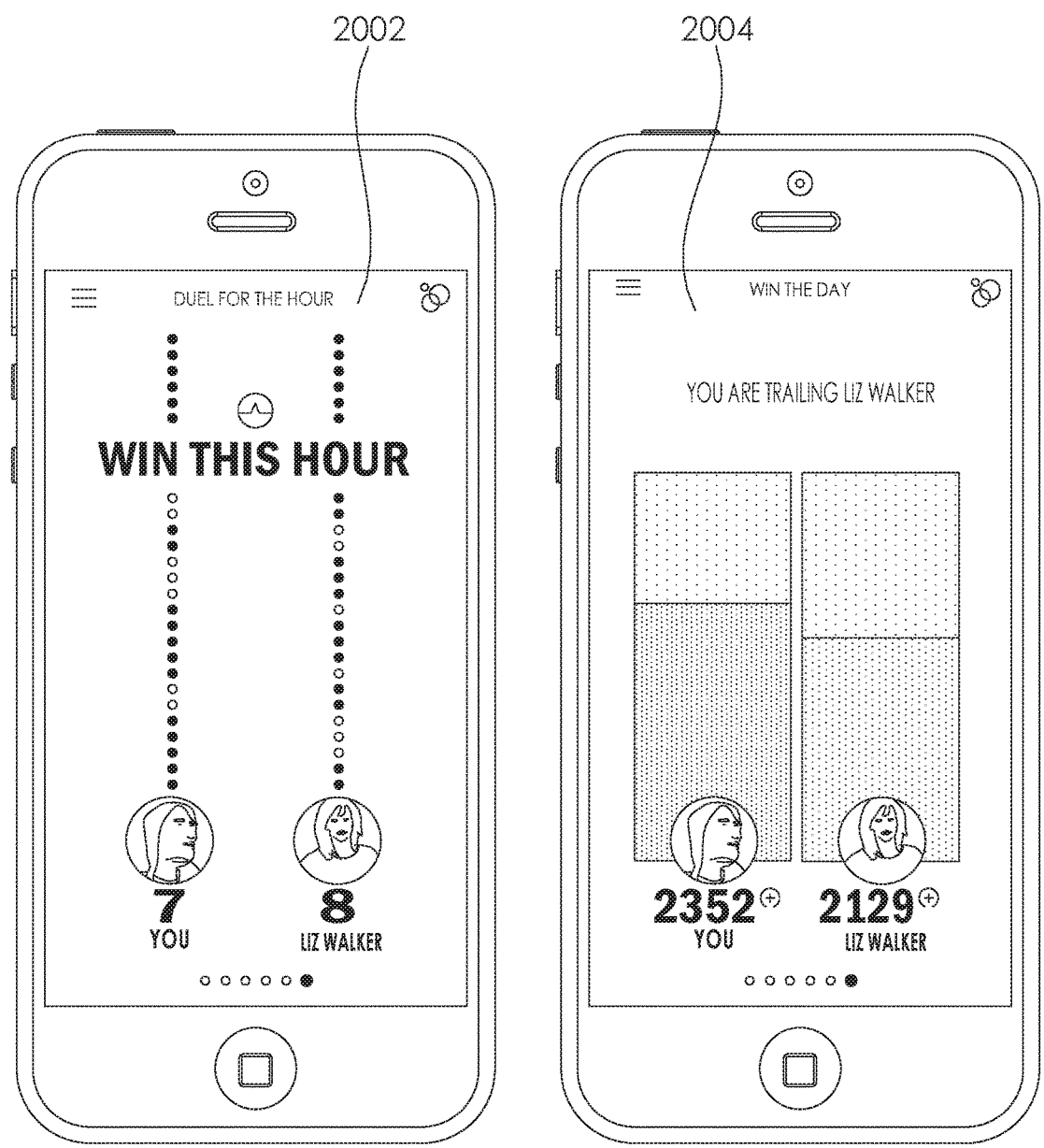

FIG. 20 illustrates user interface screens that show the state of challenges. User interface screen 2002 may be used during an hour by hour challenge. A row of dots or icons are shown above each user. Shading or colors may be used to indicate which user achieved the most energy expenditure points during the hour. For example, a loss may be represented with a light shade or first color, a tie may be represented with a medium shade or second color, and a win may be represented with a dark shade or third color. As another example, user interface screen 2004 may be used during a day challenge. Each user's point total may be represented with appropriately coloring or shading a corresponding portion of a column or row of the user interface.

Aspects described herein may be equally used with or applied to other types of activities beyond running, walking, and other step-oriented exercises. For example, data for skiing, jumping rope, weightlifting and the like may be represented by and processed using the features described herein. In particular, energy expenditure point values may be determined from any type of exercise from which an amount of calories burned may be measured or determined (e.g., according to the formulas and algorithms discussed above).

CONCLUSION

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:
1. A computer-implemented method comprising:
obtaining, by a computing device and from one or more sensors, movement data of a first user along a plurality of axes for a first time period and a second time period;
for each time period, classifying, based at least on a type of the one or more sensors, the movement data of the first user into one of a plurality of predefined activity categories;
calculating, based upon the movement data and the activity category the movement data was classified into, a first energy expenditure value for the first time period and a second energy expenditure value for the second time period;
receiving movement data of a second user along a plurality of axes for a third time period and a fourth time period;
for each time period, classifying the movement data of the second user into one of the plurality of predefined activity categories;
calculating an energy expenditure value for the third time period and the fourth time period based upon the movement data and the activity category the movement data was classified into:
determining one or more derivatives of the energy expenditure values obtained during a unitary time frame that includes the first time period and the second time period to determine a first energy expenditure intensity value;

determining the energy expenditure values obtained during the time frame that includes the third time period and the fourth time period to obtain a second energy expenditure intensity value; and displaying, using the computing device, a representation of the determined energy expenditure values and representations of the first energy expenditure intensity value and the second energy expenditure intensity value.

2. The method of claim 1, wherein classifying the movement data of the first user into one of a plurality of predefined activity categories further comprises:

determining a location of the one or more sensors; and classifying, based in part on the location of the one or more sensors, the movement data of the first user into one of the plurality of predefined activity categories.

3. The method of claim 1, wherein displaying a representation of the first energy expenditure intensity value further comprises:

visually modifying a portion of a user interface to indicate the first energy expenditure intensity value.

4. The method of claim 1, wherein the representation of the first and second energy expenditure intensity values comprises a color variable.

5. The method of claim 1, wherein the representation of the determined energy expenditure values comprises a size variable.

6. The method of claim 1, further comprising:

determining whether the energy expenditure intensity value for the first user is greater than the energy expenditure intensity value for the second user.

7. The method of claim 6, further comprising:

transmitting an electronic signal to a first electronic device associated with the first user and a second electronic device associated with the second user, indicative of whether the energy expenditure intensity value for the first user is greater than the energy expenditure intensity value for the second user.

8. The method of claim 6, further comprising:

visually modifying one or more virtual objects representing a time period within the time frame based on the determined energy expenditure values.

9. An apparatus comprising:

one or more processors; and memory storing instructions that, when executed by the one or more processors, cause the apparatus at least to:

obtain, from one or more sensors, movement data of a first user along a plurality of axes for a first time period and a second time period;

for each time period, classify, based at least on a type of the one or more sensors, the movement data of the first user into one of a plurality of predefined activity categories;

calculate, based upon the movement data and the activity category the movement data was classified into, a first energy expenditure value for the first time period and a second energy expenditure value for the second time period;

receive movement data of a second user along a plurality of axes for a third time period and a fourth time period;

for each time period, classify, based at least on a type of the one or more sensors, the movement data of the second user into one of the plurality of predefined activity categories;

calculate an energy expenditure value for the third time period and the fourth time period based upon the movement data and the activity category the movement data was classified into;

determine one or more derivatives of the energy expenditure values obtained during a unitary time frame that includes the first time period and the second time period to determine a first energy expenditure intensity value;

determine the energy expenditure values obtained during the time frame that includes the third time period and the fourth time period to obtain a second energy expenditure intensity value; and display a representation of the determined energy expenditure values and a representation of the first energy expenditure intensity value and the second energy expenditure intensity value.

10. The apparatus of claim 9, wherein the instructions, when executed, further cause the apparatus to:

transmit a communication inviting one or more other users to participate in an activity challenge.

11. The apparatus of claim 9, wherein the instructions, when executed, further cause the apparatus to display the representation of the first energy expenditure intensity value by visually modifying a portion of a user interface to indicate the first energy expenditure intensity value.

12. The apparatus of claim 9, wherein the instructions, when executed, further cause the apparatus to:

determine whether the energy expenditure intensity value for the first user is greater than the energy expenditure intensity value for the second user.

13. The apparatus of claim 12, wherein the instructions, when executed, further cause the apparatus to:

transmit an electronic signal to a first electronic device associated with the first user and a second electronic device associated with the second user, indicative of whether the energy expenditure intensity value for the first user is greater than the energy expenditure intensity value for the second user.

14. A non-transitory computer readable medium storing executable instructions that, when executed, cause an apparatus at least to:

obtain, from one or more sensors, movement data of a first user along a plurality of axes for a first time period and a second time period;

for each time period, classify, based at least on a type of the one or more sensors, the movement data of the first user into one of a plurality of predefined activity categories;

calculate, based upon the movement data and the activity category the movement data was classified into, a first energy expenditure value for the first time period and a second energy expenditure value for the second time period;

receive movement data of a second user along a plurality of axes for a third time period and a fourth time period;

for each time period, classify the movement data of the second user into one of the plurality of predefined activity categories;

calculate an energy expenditure value for the third time period and the fourth time period based upon the movement data and the activity category the movement data was classified into;

determine one or more derivatives of the energy expenditure values obtained during a unitary time frame that includes the first time period and the second time period to determine a first energy expenditure intensity value;

determine the energy expenditure values obtained during the time frame that includes the third time period and the fourth time period to obtain a second energy expenditure intensity value; and display a representation of the determined energy expenditure values and a representation of the first energy expenditure intensity value and the second energy expenditure intensity value.

15. The non-transitory computer readable medium of claim 14, wherein the executable instructions, when executed, further cause the apparatus to display the representation of the first energy expenditure intensity value by visually modifying a portion of a user interface to indicate the first energy expenditure intensity value.

16. The non-transitory computer readable medium of claim 14, wherein the representation of the first and second energy expenditure intensity values comprises a color variable.

17. The non-transitory computer readable medium of claim 14, wherein the representation of the determined energy expenditure values comprises a size variable.

* * * * *